US008287598B1

(12) United States Patent
Doty

(10) Patent No.: US 8,287,598 B1
(45) Date of Patent: Oct. 16, 2012

(54) TRUE SPINAL MOTION PRESERVING, SHOCK ABSORBING, INTERVERTEBRAL SPINAL DISC PROSTHESIS

(75) Inventor: Keith L. Doty, Gainesville, FL (US)

(73) Assignee: TrueMotion Spine, Inc., Alachua, FL (US)

( * ) Notice: Subject to any disclaimer, the term of this patent is extended or adjusted under 35 U.S.C. 154(b) by 0 days.

(21) Appl. No.: 13/311,135

(22) Filed: Dec. 5, 2011

(51) Int. Cl.
A61F 2/44 (2006.01)

(52) U.S. Cl. ........................................... 623/17.16

(58) Field of Classification Search ..... 623/17.11–17.16
See application file for complete search history.

(56) References Cited

U.S. PATENT DOCUMENTS

| 4,309,777 A | 1/1982 | Patil |
| 4,349,921 A | 9/1982 | Kuntz |
| 4,595,663 A | 6/1986 | Krohn et al. |
| 4,714,469 A | 12/1987 | Kenna |
| 4,759,766 A | 7/1988 | Buettner-Janz et al. |
| 4,759,769 A | 7/1988 | Hedman et al. |
| 4,846,840 A | 7/1989 | Leclercq et al. |
| 4,863,476 A | 9/1989 | Shepperd |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,997,432 A | 3/1991 | Keller |
| 5,002,576 A | 3/1991 | Fuhrmann et al. |
| 5,024,670 A | 6/1991 | Smith et al. |
| 5,037,438 A | 8/1991 | Davidson |
| 5,047,055 A | 9/1991 | Bao et al. |
| 5,071,437 A | 12/1991 | Steffee |
| 5,080,675 A | 1/1992 | Lawes et al. |
| 5,258,031 A | 11/1993 | Salib et al. |
| 5,258,043 A | 11/1993 | Stone |
| 5,306,307 A | 4/1994 | Senter et al. |
| 5,306,308 A | 4/1994 | Gross et al. |
| 5,306,309 A | 4/1994 | Wagner et al. |
| 5,306,412 A | 4/1994 | Whitehouse et al. |

(Continued)

FOREIGN PATENT DOCUMENTS

WO        WO-94/04100 A1    3/1994

(Continued)

OTHER PUBLICATIONS

Bao, Q.-B. et al., "Artificial disc technology," *Neurosurgical Focus*, American Association of Neurological Surgeons, Oct. 2000, pp. 1-7, vol. 9, No. 4.

(Continued)

*Primary Examiner* — Eduardo C Robert
*Assistant Examiner* — Atiya Mahmud
(74) *Attorney, Agent, or Firm* — Saliwanchik, Lloyd & Eisenchenk

(57) ABSTRACT

A modular spinal disc prosthesis, with up to three independent rotational and up to three independent translational degrees-of-freedom. The prosthesis can maintain non-separable, and non-restrictive, mechanical linkage by establishing a linked series of kinematic pairs between components. Embodiments can include a superior plate, fixedly attached to a superior vertebra in an FSU that links to a planar pair, which links to an orthogonal prismatic pair, which links to a spherical pair, which links to an inferior plate that is fixedly attached to an inferior vertebra of an FSU, completing the jointed kinematic chain. The subject invention can enforce the kinematic constraints to realize the kinematic pairs and can also limit the range of operation of the degrees of freedom for each pair. A surrounding, protective boot can be used to isolate the elements of the invention.

75 Claims, 15 Drawing Sheets

U.S. PATENT DOCUMENTS

| | | | |
|---|---|---|---|
| 5,314,477 A | 5/1994 | Marnay | |
| 5,314,478 A | 5/1994 | Oka et al. | |
| 5,320,644 A | 6/1994 | Baumgartner | |
| 5,401,269 A | 3/1995 | Büttner-Janz et al. | |
| 5,415,704 A | 5/1995 | Davidson | |
| 5,425,773 A | 6/1995 | Boyd et al. | |
| 5,458,642 A | 10/1995 | Beer et al. | |
| 5,674,296 A | 10/1997 | Bryan et al. | |
| 5,676,701 A | 10/1997 | Yuan et al. | |
| 5,782,832 A | 7/1998 | Larsen et al. | |
| 5,827,328 A | 10/1998 | Buttermann | |
| 5,865,846 A | 2/1999 | Bryan et al. | |
| 6,001,130 A | 12/1999 | Bryan et al. | |
| 6,019,792 A | 2/2000 | Cauthen | |
| 6,156,067 A | 12/2000 | Bryan et al. | |
| 6,179,874 B1 | 1/2001 | Cauthen | |
| 6,315,797 B1 | 11/2001 | Middleton | |
| 6,368,350 B1 | 4/2002 | Erickson et al. | |
| 6,395,032 B1 | 5/2002 | Gauchet | |
| 6,419,706 B1 | 7/2002 | Graf | |
| 6,626,943 B2 | 9/2003 | Eberlein et al. | |
| 6,645,248 B2 | 11/2003 | Casutt | |
| 6,656,224 B2 | 12/2003 | Middleton | |
| 6,669,732 B2 | 12/2003 | Serhan et al. | |
| 6,682,562 B2 | 1/2004 | Viart et al. | |
| 6,726,721 B2 | 4/2004 | Stoy et al. | |
| 6,733,532 B1 | 5/2004 | Gauchet et al. | |
| 6,736,850 B2 | 5/2004 | Davis | |
| 6,740,118 B2 | 5/2004 | Eisermann et al. | |
| 6,749,635 B1 | 6/2004 | Bryan | |
| 6,770,095 B2 | 8/2004 | Grinberg et al. | |
| 6,802,867 B2 | 10/2004 | Manasas et al. | |
| 6,827,740 B1 | 12/2004 | Michelson | |
| 6,833,006 B2 | 12/2004 | Foley et al. | |
| 6,960,232 B2 | 11/2005 | Lyons et al. | |
| 6,964,686 B2 | 11/2005 | Gordon | |
| 6,966,929 B2 | 11/2005 | Mitchell | |
| 6,981,989 B1 | 1/2006 | Fleischmann et al. | |
| 6,989,032 B2 | 1/2006 | Errico et al. | |
| 6,994,727 B2 | 2/2006 | Khandkar et al. | |
| 7,001,433 B2 | 2/2006 | Songer et al. | |
| 7,011,685 B2 | 3/2006 | Arnin et al. | |
| 7,014,658 B2 | 3/2006 | Ralph et al. | |
| 7,022,138 B2 | 4/2006 | Mashburn | |
| 7,022,139 B2 | 4/2006 | Errico et al. | |
| 7,044,969 B2 | 5/2006 | Errico et al. | |
| 7,048,763 B2 | 5/2006 | Ralph et al. | |
| 7,060,100 B2 | 6/2006 | Ferree et al. | |
| 7,066,960 B1 | 6/2006 | Dickman | |
| 7,101,400 B2 | 9/2006 | Thramann et al. | |
| 7,122,055 B2 | 10/2006 | Ralph et al. | |
| 7,156,876 B2 | 1/2007 | Moumene et al. | |
| 7,163,559 B2 | 1/2007 | Errico et al. | |
| 7,186,268 B2 | 3/2007 | Errico et al. | |
| 7,195,644 B2 | 3/2007 | Diaz et al. | |
| 7,198,643 B2 | 4/2007 | Zubok et al. | |
| 7,208,014 B2 | 4/2007 | Ralph et al. | |
| 7,214,244 B2 | 5/2007 | Zubok et al. | |
| 7,223,290 B2 | 5/2007 | Errico et al. | |
| 7,258,699 B2 | 8/2007 | Errico et al. | |
| 7,261,739 B2 | 8/2007 | Ralph et al. | |
| 7,270,680 B2 | 9/2007 | Ralph et al. | |
| 7,270,681 B2 | 9/2007 | Cauthen | |
| 7,273,496 B2 | 9/2007 | Mitchell | |
| 7,276,082 B2 | 10/2007 | Zdeblick et al. | |
| 7,291,171 B2 | 11/2007 | Ferree | |
| 7,314,487 B2 | 1/2008 | Ralph et al. | |
| 7,316,714 B2 | 1/2008 | Gordon et al. | |
| 7,331,994 B2 | 2/2008 | Gordon et al. | |
| 7,331,995 B2 | 2/2008 | Eisermann et al. | |
| 7,338,525 B2 | 3/2008 | Ferree | |
| 7,361,192 B2 | 4/2008 | Doty | |
| 7,442,211 B2 | 10/2008 | de Villiers et al. | |
| 7,531,001 B2 | 5/2009 | de Villiers et al. | |
| 7,582,115 B2 | 9/2009 | Weber | |
| 7,695,516 B2 | 4/2010 | Zeegers | |
| 7,713,302 B2 | 5/2010 | Ralph et al. | |
| 7,731,754 B2 | 6/2010 | de Villiers et al. | |
| 7,758,645 B2 | 7/2010 | Studer | |
| 7,771,477 B2 | 8/2010 | Ralph et al. | |
| 7,799,080 B2 | 9/2010 | Doty | |
| 7,927,375 B2 | 4/2011 | Doty | |
| 2002/0111681 A1 | 8/2002 | Ralph et al. | |
| 2003/0014110 A1 | 1/2003 | Ralph et al. | |
| 2003/0014112 A1 | 1/2003 | Ralph et al. | |
| 2004/0167626 A1 | 8/2004 | Geremakis et al. | |
| 2004/0260396 A1 | 12/2004 | Ferree et al. | |
| 2005/0015152 A1 | 1/2005 | Sweeney | |
| 2005/0192670 A1 | 9/2005 | Zubok et al. | |
| 2005/0234555 A1 | 10/2005 | Sutton et al. | |
| 2005/0240270 A1 | 10/2005 | Zubok et al. | |
| 2005/0273169 A1 | 12/2005 | Purcell | |
| 2006/0036324 A1 | 2/2006 | Sachs et al. | |
| 2006/0136062 A1 | 6/2006 | DiNello et al. | |
| 2006/0235525 A1 | 10/2006 | Gil et al. | |
| 2006/0235529 A1 | 10/2006 | Ralph et al. | |
| 2007/0150062 A1 | 6/2007 | Zubok et al. | |
| 2008/0015699 A1 | 1/2008 | Voydeville | |
| 2008/0021557 A1 | 1/2008 | Trieu | |
| 2008/0027547 A1 | 1/2008 | Yu et al. | |
| 2008/0058940 A1 | 3/2008 | Wu et al. | |
| 2008/0065211 A1 | 3/2008 | Albert et al. | |
| 2008/0077242 A1 | 3/2008 | Reo et al. | |
| 2008/0077244 A1 | 3/2008 | Robinson | |
| 2008/0077246 A1 | 3/2008 | Fehling et al. | |
| 2010/0070033 A1 | 3/2010 | Doty | |
| 2010/0076558 A1 | 3/2010 | de Villiers et al. | |
| 2010/0324688 A1 | 12/2010 | Doty | |
| 2011/0160859 A1 | 6/2011 | Doty | |

FOREIGN PATENT DOCUMENTS

| | | |
|---|---|---|
| WO | WO-2004/054477 A1 | 7/2004 |
| WO | WO-2007/076194 A2 | 7/2007 |
| WO | WO-2010/147795 A2 | 12/2010 |

OTHER PUBLICATIONS

Bao, Q-B. et al., "The artificial disc: theory, design and materials," *Biomaterials*, 1996, pp. 1157-1167, vol. 17, No. 12.

Bogduk, N. et al., "Biomechanics of the cervical spine. I: Normal kinematics," *Clinical Biomechanics*, 2000, pp. 633-648, vol. 15.

Bogduk, N. et al., "A biological basis for instantaneous centres of rotation of the vertebral column," *Proceedings of the Institution of Mechanical Engineers*, 1995, pp. 177-183, vol. 209.

Bogduk et al., *Clinicial Anatomy of the Lumbar Spine*, ISBN 0-443-03505-9, 1987, Churchill-Livingstone Melbourne Edinburgh London New York.

Büttner-Jantz, et al., *The Artificial Disc*, ISBN 3-540-41779-6, 2003, Springer-Verlag, Berlin Heidelberg New York.

Van Mameren, H. et al., "Cervical Spine Motion in the Sagittal Plane II: Position of Segmental Averaged Instantaneous Centers of Rotation—A Cineradiographic Study," *Spine*, 1992, pp. 467-474, vol. 17, No. 5.

Mow et al., *Basic Orthopaedic Biomechanics*, Lippincott-Raven Pub., N.Y., 2$^{nd}$ Edition, 1997.

Panjabi, M.M. "Instantaneous Center of Rotation and Instability of the Cervical Spine: A Clinical Study," *Spine*, Mar. 1997, pp. 647-648, vol. 22, No. 6.

Panjabi, M.M. et al., "Articular Facets of the Human Spine: Quantitative Three-Dimensional Anatomy," *Spine*, 1993, pp. 1298-1310, vol. 18, No. 10.

Yoganandan, N. et al., "Chapter 5—Biomechanics of the Cervical Spine," *Principles of Spinal Surgery*, McGraw-Hill, 1996, pp. 69-83.

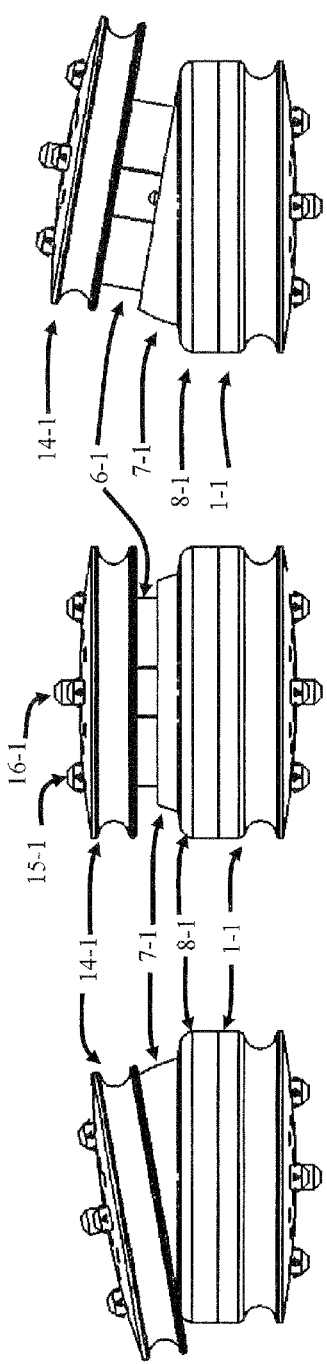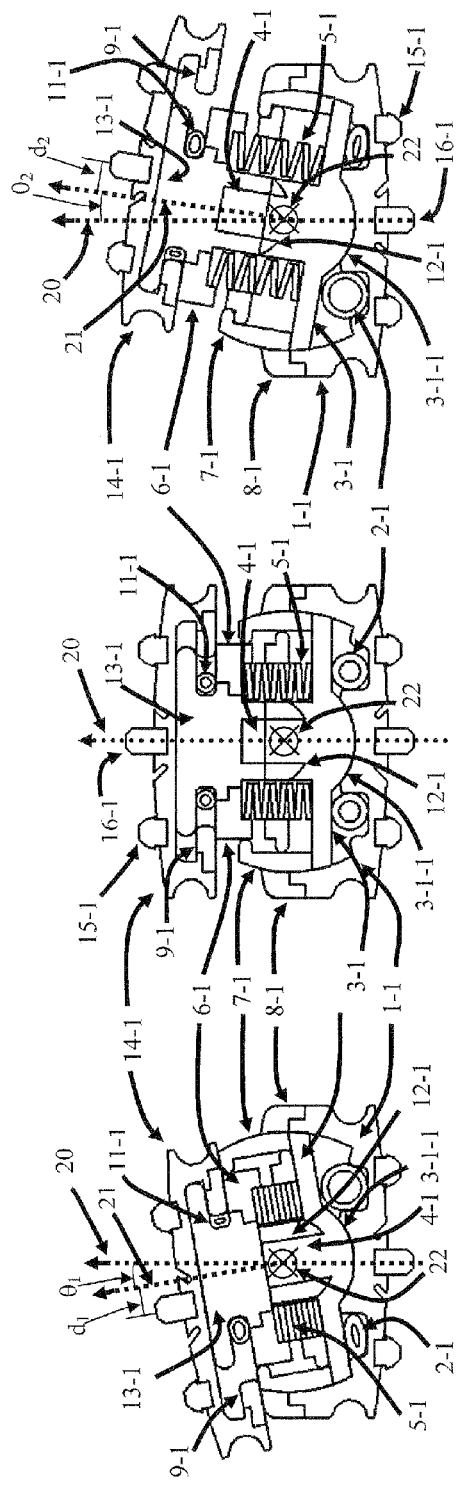

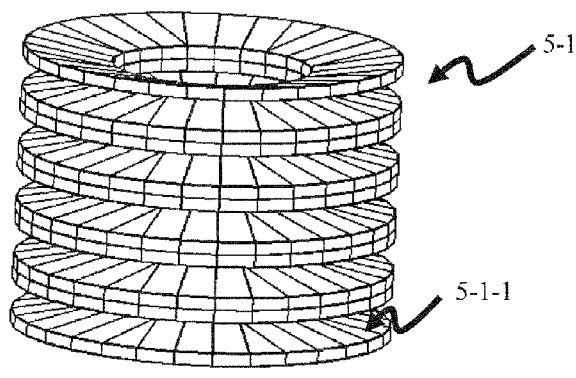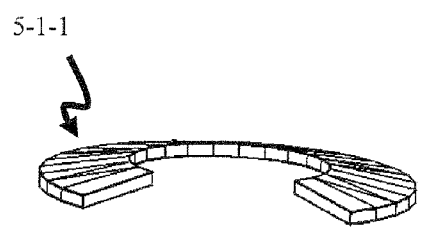
FIG. 22A   FIG. 22B
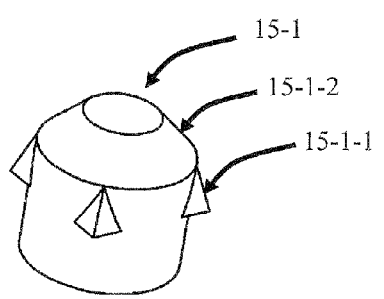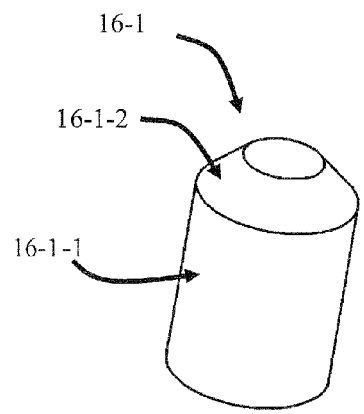
FIG. 23A   FIG. 23B

TRUE SPINAL MOTION PRESERVING, SHOCK ABSORBING, INTERVERTEBRAL SPINAL DISC PROSTHESIS

BACKGROUND OF INVENTION

Spinal disc herniation, a common ailment, often induces pain, as well as neurologically and physiologically debilitating processes, for which relief becomes paramount. If conservative treatments fail, the more drastic measures of discectomies and spinal fusion may be indicated. The latter treatment, while providing short term relief, limits spinal mobility and often leads to excessive forces on facet joints adjacent to the fusion and may create further problems over time. Drastic treatments are usually unable to restore normal disc function. The loss of disc function has led to a number of disc prostheses that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474). This motion varies widely between functional spinal units on an individual spine and between individuals and can depend on age, time-of-day, and the general health and condition of the intervertebral discs, facet joints and other components of the FSU and spine. A moving IAR means that the superior vertebra can both rotate and translate while moving with respect to the inferior vertebra of an FSU. Natural spinal motions place severe requirements on the design of a prosthetic disc; simple rotational joints are not able to meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

Researchers have attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", Clinical Biomechanics, Elsevier, 15 (2000) 633-648; and Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474), this restricted motion does not correspond to the natural motion of the vertebrae, either for sagittal plane motion or for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability and excessive facet loading.

As a further elaboration on the many ball-and-socket configurations, consider Salib et. al. (U.S. Pat. No. 5,258,031) an example of previous efforts to address this problem. The Salib et al. ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit.

Currently known devices appear to have similar motion and instability limitations, such as the rocker arm device disclosed by Cauthen (U.S. Pat. Nos. 6,019,792; 6,179,874; 7,270,681), the freely moving sliding disc cores found in the Bryan et al. patents (U.S. Pat. Nos. 5,674,296; 5,865,846; 6,001,130; and 6,156,067) and the SB Charité™ prosthesis, as described by Búttner-Jantz K., Hochschuler S. H., McAfee P. C. (Eds), The Artificial Disc, ISBN 3-540-41779-6 Springer-Verlag, Berlin Heidelberg New York, 2003; and U.S. Pat. No. 5,401,269; and Buettner-Jantz et al. U.S. Pat. No. 4,759,766). In addition, the sliding disc core devices of the Bryan et al. and SB Charité™ devices do not appear to permit natural motion of the joint for any fixed shape of the core.

With the above described prosthetic devices, when the FSU extends, the prosthesis's sliding core, in some cases, generates unnatural constraining forces on the FSU by restricting closure of the posterior intervertebral gap in the FSU. Further, the core does not mechanically link the upper and lower plates of the prosthesis and is unable to accommodate the changing intervertebral gap throughout the range of motion. Such conditions can contribute to prosthetic disc spondylolisthesis and/or transmission of large forces through the prosthesis not normally experienced with nominal loads. In general, unconstrained or over-constrained relative motion between the two plates in a prosthetic disc can contribute to FSU instability over time.

Various means of incorporating uniform, predictable, and kinematically restricted, relative lateral translation motion between plates without joint separation have been proposed, for example, by Zeegers in U.S. Pat. No. 7,695,516. Uniform, predictable two dimensional, and kinematically restricted, relative translational motion along a frontal axis from anterior to posterior and an orthogonal sagittal axis from left lateral to right lateral without joint separation has been proposed by Doty (U.S. Pat. Nos. 7,361,192; 7,799,080; 7,927,375 and U.S. Patent application US2010/0324688A1). Vertical translations relate closely with static and dynamic load handling prostheses and will be discussed next.

Current prosthetic disc technology appears to be limited in static and dynamic load handling capability. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the changing intervertebral gap requirements during motion, and may generate excessive reaction forces on the spine during flexion, forces that can potentially produce extra stress on facet joints and affect mobility.

More recent attempts to provide dynamic and static loading capability is taught in the series of patents by Ralph et al. (U.S. Pat. Nos. 6,645,249; 6,863,688; 6,863,688; 7,014,658; 7,048,763; 7,122,055; 7,208,014; 7,261,739; 7,270,680; 7,314,487; and 7,713,302) wherein the force restoring mechanism begins with a multi-pronged domed spring between two plates followed by a wave-washer, then ending with a spiral grooved Belleville spring as the force restoring element. The multi-pronged domed spring employs a ball-and-socket arrangement on the upper plate and allows relative rotations between the spring-lower plate and the upper plate. This arrangement, during nominal FSU operation, places moments of force on the spring that tend to distort the spring and place high stresses on the set screws holding the spring down. The effects of force moments on the prongs and the dome spring is mitigated by later designs where various modifications of the spring element, as for example the spiral Belleville washer in U.S. Pat. No. 7,270,680, provides the spring more resilience to moments of force. As taught in these patents, the motion of the upper plate is limited to compression and rotation. Lateral and sagittal translations are not accommodated and so general motion in the FSU is not enabled by the device.

The work of Errico et al. (U.S. Pat. Nos. 6,989,032; 7,022,139; 7,044,969; 7,163,559; 7,186,268; 7,223,290; and 7,258,699) elaborates on the mechanical design of the patents of Ralph et al. A specially designed Belleville type washer provides a restoring force to compressions. Rotations of the superior plate of the device in a fixed ball-and-socket arrangement transfers moments of force about the washer central axis to a rigid structure. It is notable that the instruction in these designs specifically proscribes lateral motions (sagittal and lateral translation). Errico et al. employ a taper attached to the ball to limit rotation angles. De Villiers (U.S. Pat. No. 7,442,211) also describes how to control rotation angle limits using an annular joint stop on an ovate core. The rotational joint stop element taught here can apply non-uniform angle limits on rotations within a socket as well uniform rotation angle limits. It can be observed that in the De Villiers' device, rotations about the major axis of the ellipsoid are unrestricted.

Another approach to incorporate dynamic and static force response is taught by Gauchet (U.S. Pat. Nos. 6,395,032; 6,527,804; 6,579,320; 6,582,466; 6,582,468; and 6,733,532) wherein a hydraulic system provides shock absorption by means of a cushion between two plates contained within sealed flexible titanium bellows. Gauchet suggests the bellows can be designed to accommodate lateral forces and axial rotation that is permitted by the cushion, which, to allow sliding motion, is not attached to at least one plate. The titanium bellows can accommodate some axial rotations, but do not seem suitable for other rotations, which can cause excessive stresses on the bellows. A cushion internal to the cylinder, being flexible and not attached to at least one plate, can accommodate any rotation (U.S. Pat. Nos. 6,582,466 and 6,733,532).

Fleishman et al. in U.S. Pat. Nos. 6,375,682 and 6,981,989 utilize hydraulic action coupled with a flexible bellows to mitigate sudden forces. The bellows concept is similar to that of Gauchet.

Eberlein et al. (U.S. Pat. No. 6,626,943) utilize a fiber ring to enclose a flexible element. The forces and moments of force are absorbed by the ring and the flexible element. Other inventions teach a fiber ring type concept as well, namely, Casutt in U.S. Pat. No. 6,645,248. Diaz et al. (U.S. Pat. No. 7,195,644) also uses a membrane and enclosed cushioning material in their ball and dual socket joint design. Diaz also instructs that discontinuous segments of a connecting elastomer membrane around the periphery of a prosthesis can act as a plurality of elastic bands. The device taught in this invention can use a tough, fiber reinforced boot to provide a function similar to that of a fiber ring but with the added capability to seal in fluids/gases/gels within the device or seal out fluids and gases from interacting with the movable joints within the structure.

Middleton suggests a variety of machined springs as the central component of a disc prosthesis in U.S. Pat. Nos. 6,136,031; 6,296,664; 6,315,797; and 6,656,224. The spring is notched to allow static and dynamic response primarily in the axial direction of the spring. Lateral and sagittal translations and general rotations may be problematic in these designs. The ability of such springs to tolerate off-axis compression forces may also be problematic.

Gordon instructs deforming a machined spring as the principle separating and force management component (U.S. Pat. Nos. 6,579,321; 6,964,686; and 7,331,994). In U.S. Pat No. 7,316,714 the emphasis is on posterior insertion of a disc prosthesis that can provide appropriate motion. However, this latter design does not appear to accommodate static and dynamic loading and there appears to be no accommodation for lateral and sagittal translations.

Zubok instructs in U.S. Pat. No. 6,972,038 (Column 3; Line 35) that " . . . the present invention contemplates that with regard to the cervical anatomy, a device that maintains a center of rotation, moving or otherwise, within the disc space is inappropriate and fails to properly support healthy motion." This statement may be true as long as translations within the prosthesis mechanism do not adequately compensate for the total motion induced by an IAR outside of the disc space. The current invention, however, by sufficient means of three linearly independent translational degrees of freedom and three independent rotational degrees of freedom (for example, roll-pitch-yaw) within the FSU disc space, can generate any equivalent relative motion of the superior vertebra relative to an inferior vertebra within an FSU whose motion is generated by a moving IAR outside or inside the disc space. Further, the mechanisms of the current invention that generate the equivalent motion are so coupled that they can prevent separation of any moving elements of the prosthesis beyond mechanically programmed joint limits.

Several approaches by Ferree (U.S. Pat. Nos. 6,419,704; 6,706,068; 6,875,235; 7,048,764; 7,060,100; 7,201,774; 7,201,776; 7,235,102; 7,267,688; 7,291,171; and 7,338,525) primarily instruct how to cushion a prosthetic FSU in various ways. An exception is U.S. Pat. No. 6,706,068, which describes a design to perform certain kinematic motions of a disc prosthesis without dynamic or static cushioning support, and U.S. Pat. No. 7,338,525, which instructs on disc prosthesis anchoring.

Aebi incorporates essentially a hook joint (orthogonal revolute joints) in EP1572038B1 as the means for realizing motion. While the Aebi arrangement of revolute joints does allow for sagittal and lateral rotations, it does not appear to engage in the remaining four degrees of freedom in three-space, namely, sagittal, lateral, and axial translations along with axial rotations. Mitchell (U.S. Pat. No. 7,273,496B2) uses two revolute joints by means of orthogonal cylinders placed on top of each other and embedded as a crossbar element between plates with cavities for accepting the crossbar. This device has the limitations of motion similar to the Aebi device and the further limitation of not kinematically chaining the two plates together with the crossbar.

Khandkar (U.S. Pat. No. 6,994,727 B2) provides two orthogonal convex curvate bearing structures, with offset cylindrical radii of curvature, placed between the plates. An insert, with orthogonal, variable-curvature concave bearing surfaces, is placed between, and generally conforms to, the orthogonal convex bearings on the plates. This arrangement of bearings allows sagittal, lateral, and axial rotations of various ranges, dictated by the curvate bearing structures and the insert. The variable curvate surfaces allow some lateral and sagittal translations with FSU distractions, utilizing normal spinal forces to resist the distraction and, hence, the motion. There is no apparent control on the forces involved, so this method could lead to possible stress on other spinal joints. The inserted device is not kinematically chained to the rest of the device and can possibly be disengaged. Although, as instructed, the device is self-correcting within a limited range, tending towards a stable equilibrium established for the device in normal position. The variable curvatures result, typically, in line- and point-contact bearing manifolds that can wear the surfaces, possibly causing changes in the performance and characteristic motion of the device over time. In general, motion along the various manifold interfaces involved restricts the flexibility and adaptability of the device to accommodate other motions.

DiNello (U.S. Published Application No. 2006/0136062A1) instructs on how to adjust height and angulations of a motion disc after implantation.

Weber, in U.S. Pat. No. 7,582,115, introduces a prosthetic core which is a ball at one end and a plane at the other end that fits, respectively, into a curved socket superior plate and a plane surface inferior plate, allowing the core element to slide as well as permitting the superior plate to rotate about the ball end.

With respect to the lower vertebra in an FSU, all possible, natural loci of motion of any four non-planar, non-collinear points located in the superior vertebra define the natural workspace of an FSU. This workspace varies from one FSU to another on the spine and from one individual to another, creating considerable spinal disc prosthesis design problems.

The devices of the subject invention provide a general motion spatial mechanism. The device solves certain natural motion and shock absorbing characteristics that are problematic for a spinal disc prosthesis and offer a scalable mechanism for disc replacement without loss of general motion capabilities in the FSU.

SUMMARY OF THE INVENTION

The subject invention provides a device capable of providing mechanically-linked, relative spatial movement, with up to six-degrees of freedom. The device described herein can be utilized in a multitude of mechanical applications to provide motion capabilities. Advantageously, the devices of the subject invention can be implanted in a Functional Spinal Unit (FSU) of a patient and facilitate complex relative motion between the vertebrae of the FSU by allowing independent sagittal, lateral, and axial displacements and up to three independent rotations.

As used herein, the term operational integrity when applied to a spherical pair joint means that displacements between the centers of curvature of the involved spherical surfaces can be constrained to be approximately coincident to restrict motion of the joint to rotations about a common center of curvature, for example, point 7-1-9. The term operational integrity as used herein and applied to a planar or prismatic pair joint means that displacements between the involved surfaces of the joint can be tightly constrained to planar or one dimensional slider motion, respectively. The embodiments of the subject invention's kinematic linkage maintain operational integrity for all six degrees of freedom.

The motion elements of any particular embodiment of the spinal disc prosthesis of the subject invention are typically operated and controlled by the muscles and ligaments of the spine, when implanted in an FSU. Spinal muscles and ligaments can drive the spring/cushion-damping system and resultant motion of the prosthesis. The kinematic generality of the motion capabilities of the subject invention prosthesis, allows natural movements of any FSU along a spine in which an appropriately dimensioned and parameterized prosthesis is placed. Specifically, with appropriate dimensioning and parameter adjustments, the workspace embodiments of the subject invention can be tailored to meet the natural or clinical motion requirements of any FSU along the spine.

The dimensions of the subject device vary depending upon intended use, minimum and maximum compression and extension and other factors known to those with skill in the art. For example, embodiments utilized within the spine of a patient can require different dimensions depending upon intended location. Implantation towards the more cranial end of the spine can necessitate smaller dimensions than would implantation nearer the caudal end. In a particular embodiment, a cervical spine device of the subject invention is between approximately 6 mm and approximately 10 mm in height when the device is in a fully compressed state and between approximately 8 mm and approximately 10 mm in a fully extended state, measured between the superior surface of the superior plate and the inferior surface of the inferior plate. In another particular embodiment, the diameter is between approximately 12 mm to approximately 18 mm.

The devices of the invention are not limited to cervical applications. The devices can be scaled and parameterized for application anywhere on a spine or in other medical or non-medical mechanical applications requiring a general, compact, passive connection between elements that move relative to each other with one, and up to six, independent degrees of freedom. Several significant design features of the invention enable such a compact design and are discussed in the ensuing description.

In one embodiment, a superior plate fixes to a superior vertebra and an inferior plate fixes to an inferior vertebra of a Functional Spinal Unit (FSU). The superior surface of a superior plate and the inferior surface of an inferior plate each can have a central guide pin and, positioned about the surfaces of the plates, a plurality of "peripheral" guide pins and micro-orifices. The guide pins contribute to the immediate stability of a spinal arthroplasty, while the micro-orifices encourage longer term bone fusion of the vertebrae with the plates. The guide pins can also be configured with barbs, cavities, channels, tunnels, holes, indents or other types of openings, depressions, extensions, or other structures to encourage bone fusion. Tolerances allowed for pre-insertion-drilled pilot holes for guide pins, whose insertion ends can be chamfered or conical frustums, can be so selected to produce secure, tight insertion of the peripheral guide pins and a low friction insertion of the central guide pin.

The location of a central guide pin on each plate, within the field where the natural disc connects to the vertebrae of an FSU, can be critical to gain optimal mobility within the FSU. Hence, the central pilot hole can be drilled accordingly. A central guide pin on each plate can be slightly longer than the other guide pins. In one embodiment, the central guide pin is approximately 0.5 mm longer, to ensure partial insertion of the center guide pin before the others. The pilot holes for the other guide pins can then be easily found by rotating the device about the central guide pins, which, perforce, must align along the same axis in the neutral position of the FSU. This axis becomes the central axis 20 of the device in the neutral position (refer to FIG. 7B and FIG. 8).

In a further embodiment, a guide pin extends between approximately 0.5 mm to approximately 1 mm taller than the largest peripheral guide pin in spinal arthroplasty applications. Guide pins can comprise a material that easily slides against, or has minimal friction with, cancellous bone. In U.S. Pat. No. 7,060,100, Ferree instructs the use of a four-armed conic shaped spike with holes to help attach plates to vertebrae. In a much earlier work, disclosed in WO 1994/04100, Mazda instructs the use of conical fusion spikes with side edges that allow a wrench to grip the cones in order to screw them into the plates. The use of guiding pins for secure, accurate placement of a prosthesis is disclosed in U.S. patent application Ser. No. 13/157,539 (Doty) filed Jun. 10, 2011, and is incorporated by reference herein in its entirety, including any figures, tables or drawings. The length of a central guide pin and/or other guide pins can vary depending upon a variety of factors that would be understood by a person with skill in the art.

As viewed externally, embodiments of the subject invention can approximate a variety of three dimensional shapes including, but is not limited to, segments of a sphere, an ovoid, a rounded-corners square, and a right circular cylinder. A specific embodiment, diagramed and discussed herein (FIG. 1), has an overall right circular cylindrical shape The devices of the subject invention can achieve up to six degrees of freedom, including up to three independent rotational degrees of freedom and up to three independent linear degrees of freedom, such that the device of the subject invention can facilitate sagittal, lateral, and axial vertebral displacements and general rotations when utilized in spinal arthroplasty. The interior mechanisms of the devices of the subject invention kinematically and mechanically connect or link the superior and inferior plates by means of mechanically interlocked and inseparable joint elements in a kinematic chain within the device. The superior and inferior plates themselves can be fixedly attached to the superior and inferior vertebrae in an FSU, respectively. Under nominal FSU workspace motions, all elements of the invention ideally remain mechanically linked together, yet allow completely general FSU workspace motion.

Certain embodiments of the subject invention comprise a six-degrees-of-freedom (6-DOF) modular prosthetic mechanism realized by a set of serially linked joint pairs. In one embodiment, a planar pair exists between a superior plate cavity surface and the top surface of an interior piston element, yielding two orthogonal, independent degrees of translational freedom. This planar surface can be orthogonal to the piston axis 21 (FIG. 7A, FIG. 7B, FIG. 14, and FIG. 15) of a piston element 25 (FIG. 16). In a further embodiment, a planar-retainer 9-1 prevents the head of the piston element from separating from the superior plate during planar motion of that plate and fixedly inserts into a curvate recess located around the mouth of a cavity in a superior plate 14-1 (FIG. 17), after the piston head has been inserted into that cavity.

The piston can independently travel up and down its own piston axis 21, in and out of a spherical segment shell 7-1 possessing an accommodating cylindrical cavity, and, thus, realizes a slider joint along that axis. The prismatic action of the piston can provide a third, independent translational degree of freedom, which is orthogonal to the other two when piston axis 21 of piston 25 is perpendicular to the plane of the planar pair, namely, planar surfaces 13-1-1 and 14-1-1.

In one embodiment, a spherical retainer 8-1 (FIG. 18) enforces containment of a spherical segment shell 7-1 within a socket cavity of the inferior plate. The spherical segment shell, also called the "ball", along with a rotating platform 3-1, called the "ball platform" abutting the shell's inferior surface, kinematically constrains the piston motion, limiting the range of travel of the piston's upward and downward strokes and confining at least a portion of the piston to remain within the spherical segment shell during all permitted motions. In this embodiment, the spherical segmented shell rotates within the inferior plate's socket, providing three independent degrees of rotational freedom. As a superior vertebra attached to a superior plate rotates, a spherical segment shell can rotate to accommodate the motion, rotating the cylinder and superior plate as well. The polar axis 21 of the ball 7-1 is the same as the piston axis. Spring/cushion elements denoted generically by 5 and illustrated generically in FIG. 25 can be 5-1 in FIG. 22 or 5-2 or 5-3 in FIG. 26 or 5-4 or 5-5 in FIG. 27. The ball platform 3-1, spring/cushion elements 5, piston 25, and superior plate 14-1 all rotate when the ball 7-1 rotates. A rotation cushion 2-1 can provide resistance to rotations as can a protective, tough, flexible, fiber-reinforced boot attached to the device.

Further embodiments can include installation of joint stops, by which the range of motion permitted for each of the six degrees of freedom of motion realized by the joints can be limited and/or controlled. The range of motion of the planar pair can be manipulated by the shape of the superior plate's cavity contour and/or the contour of the piston head. The strategic insertion of cushion elements or impediments along those contours can also be used to control the range of motion of the planar joint. In one embodiment, the range of motion of the piston prismatic joint, comprising cylinder 6-1 sliding in and out of cavity 7-1-2 of ball 7-1 and superior mandrel 12-1 wall segments 12-1-1 sliding along inferior mandrel 4-1 wall segments 4-1-1, can be established by several mechanisms as well, such as, for example, by spring and/or cushion elements within the cylinder's central cavity and/or the vertical placement of the slider bearings on the spherical segment shell and/or the cylinder's exterior surface and/or the placement of shock absorbing washers 26-1 (FIG. 24 and FIG. 25).

In another embodiment, rotations can be controlled by a lip or ledge near the base of the inferior plate's socket (see, for example, FIG. 7, FIG. 9, and FIG. 13). In this embodiment, the ball platform's spherical segment 3-1-1 can have the same center of curvature 22 as the ball when the device is assembled, but a much smaller radius of curvature, and can sit within socket 1-1-1 of the inferior plate 1-1. As the spherical edge 3-1-4 of the ball platform 3-1 rotates on inner spherical surface 1-1-2 of the larger socket of inferior plate 1-1, the platform that overhangs the ball 3-1-1 rotates down onto the ledges 1-1-3 and 1-1-10, stopping further rotation. The ball platform 3-1 can turn about piston axis 21 and is not prevented from doing so by the ledges. However, at maximum rotation, the rotation cushion 2-1 can have a substantial surface area contact with the underside of the ball platform and can provide some resistance to any piston axis rotation.

The depth of the ledge within the socket can dictate the rotational range of motion. In a specific embodiment, these ledges limit rotations to ±10 degrees about any axis passing through the center of curvature 22 and perpendicular to the piston axis 21. By varying the socket depth of the ledge around its periphery, non-uniform rotation limits can also be established. By way of non-limiting example, a gradual raising of the ledge by 5 degrees from the anterior section of the ledge to the left and right lateral sides and then back down 5 degrees to the posterior section could allow up to approximately 20 degrees of motion between full flexion and full extension (±10 degrees), but will limit pure lateral rotations to 5 degrees left and 5 degrees right (±5 degrees). In one embodiment, to reduce the general rotation limits, a rigid or cushioned "washer" can be fixed onto the ledge 1-1-3. The thickness of the washer dictates the slope of its upper surface so that it conforms to the ball platform's underneath planar surface 3-1-7. The washer's lower surface can match the 10 degree slope of the ledge. If the washer has a cushioned surface, or itself is a cushion element, it can compress further but could also resist further rotation motion according to the cushion's degree of compressibility.

Regardless of the orientation of the device of the subject invention within a force field (for example, gravity), the devices are capable of operating according to design because all joint pairs kinematically link together and remain functional, whether the device is in a top-bottom or bottom-top orientation. Linkage between the superior and inferior vertebra of an FSU, with the device implanted, can be established by demonstrating a stack like assembly.

In one embodiment, a superior plate 14-1 (FIG. 17) is fixedly attached to a superior vertebra of an FSU by means of central guide pins 16-1 or 16-2, peripheral guide pins 15-1 or 15-2, and/or bone fusion cavities 14-1-9. A planar retainer 9-1 can further lock the piston head 13-1 into the planar socket 14-1-2 of superior plate 14-1, ideally without hindering the relative planar motion between plate 14-1 and piston head 13-1.

In a further embodiment, illustrated in FIG. 21, cylinder 6-1 can be slid up through the cylindrical cavity of the ball 7-1, as long as the plurality of bearing raceways on the two elements align. First bearing 6-1-7 and the second bearing 7-1-4 are able to interfere with each other at maximum extension stroke of the cylinder, which can occur at full extension of the prosthesis. Planar cushions can now be mounted within the piston head raceway 13-1-3. The piston head 13-1 and superior mandrel 12-1, retained within superior plate 14-1 by retainer 9-1, can further be press fit into cylinder 6-1 at this juncture.

In a still further embodiment, rotation cushion 2-1, ball platform 3-1 and spring/cushion elements 5 are placed into the socket of the inferior plate 1-1. Finally, this subassembly is press fit into ball retainer 8-1, combining the upper and lower subassemblies together. When ball retainer 8-1 is fixedly attached to inferior plate 1-1, the entire mechanism becomes inseparable without interfering with the operation of the six degrees of freedom of movement provided between the superior plate 14-1 and the inferior plate 1-1. Finally to complete the kinematic linkage between the superior and inferior vertebrae of an FSU with the arthroplasty, inferior plate 1-1 can be fixedly attached to the inferior vertebra by means of central guide pins 16-1 or 16-2, peripheral guide pins 15-1 or 15-2, and bone fusion-cavities 1-1-9.

Embodiments of the invention implanted within an FSU are typically in a neutral position when the FSU is likewise in its neutral position. For each embodiment, this can establish the joint ranges and limits and defines a reference position for each joint. In a particular embodiment, when configured in the neutral position, the superior and inferior central guide pin axes 20 (alias: device axis; device central axis) coincide with the ball's polar axis (aliases: piston axis; cylinder axis) 21.

In one embodiment, when the device is in neutral position, the planar joint existing between piston 25 and superior plate 14-1 can permit the center of surface 14-1-1 to move, with respect to the center of piston planar surface 13-1-1 on piston head 13-1, approximately 1 mm in any direction from the center of piston planar surface 13-1-1. In this embodiment, motion of superior plate 14-1, in polar coordinates $(r, \theta)$, with origin at the center of piston planar surface 13-1-1, when the embodiment is in a neutral position, can be approximately ±1 mm in the radial direction r at any direction $\theta$ from the center with respect to a specified reference.

In a particular embodiment, flexible, toroidal cushion elements 10-1 and 11-1 (FIG. 2, FIG. 7, FIG. 8, and FIG. 14), can wrap around the "neck" 3-1-8 of piston head 13-1 to resist planar motion of the superior plate as planar retainer 9-1 partially compresses them. The amount of translation can be reduced by the tube thicknesses or compensated for by reducing the diameter of the neck. Planar cushions can be solid or tubular, the latter can be filled with compressible, or noncompressible, fluids/gases/gels which absorb energy and transfer forces to expanding the tubes to regions opposite the forces.

A superior segmented-wall mandrel 12-1 (FIG. 14) can be fixedly attached to the inferior surface of piston head 13-1. Alternatively, it can be manufactured as an integrated feature of piston head 13-1. An inferior segmented-wall mandrel element 4-1 (FIG. 10) can be fixedly attached to the ball platform 3-1, centered within cavity 3-1-3. Alternatively, it, too, can be manufactured as an integrated part of 3-1, as shown, for example, in FIG. 11. In a particular embodiment, the prismatic joint comprising the piston 25 and the ball 7-1 moves parallel to piston axis 21. As the piston 25 moves up and down, the superior and inferior mandrel's wall segments are able to slide past one another parallel to piston axis 21, as does the outer wall of cylinder 6-1 of piston 25 and inner cylindrical wall of ball 7-1. In a further embodiment, the segmented walls of the mandrel elements mesh and do not interfere with each other, the cylinder, or the spring, or other cushion elements, as they slide past one another during prismatic joint action. In yet another embodiment, chamfered, or curvate caudal, ends 12-1-2 of the superior mandrel walls assist by centering spring cushion elements as the walls move past them. With this embodiment, within the prismatic joint range, the segmented-wall mandrel elements can provide continuous columnar support for spring and cushion elements on central axis 21 of the cylinder.

Piston 25 can perform as a central, compressible and extendible hydraulic cylinder. In a further embodiment, the piston's cylinder 6-1 can incorporate a plurality of hydraulic portals 6-1-8 to allow fluid or gas flow from the cylinder chamber into, and out of, other cavities and spaces within the device during the pumping action of the piston prismatic joint. In conjunction with springs/cushion elements 5-1, the piston can provide hydraulic damping and shock absorbing capabilities to the devices of the subject invention. For instruction on hydraulic damping and the use of hydraulic portals, refer to U.S. Pat. Nos. 7,361,192, and 7,799,080 and Published Patent Application Nos. US2010/0070033, PCT/US2010/37721 and US2010/0324688A1 and U.S. Ser. No. 13/157,539 (all to Doty), which are hereby incorporated by reference in their entireties including any tables, figures or drawings therein.

As mentioned above, the wall segments of the superior and inferior mandrels can interlace and do not interfere with one another as their lateral wall-edge surfaces slide by each other with the rise and fall of the piston prismatic pair, which can include the exterior surface of the cylindrical wall 6-1-3 of 6-1 and interior cylindrical surface 7-1-3 within the ball cavity 7-1-2 of the spherical segment shell or "ball" 7-1. In one embodiment, the wall segments of the superior and inferior mandrel completely mesh into a minimum spatial occupancy at full compression and form a compact interlaced column. In a further embodiment, at maximum allowed extension, the mandrel wall segments still overlap and are never separated. In a still further embodiment, where the segmented-walls of the superior and inferior mandrels overlap, there are no wall gaps (with the exception of bearing clearances) around the circumference of the mandrel column; otherwise, there are alternating wall segments and wall gaps. Thus, no matter the axial motion, mandrel elements can provide central mechanical support for spring and/or cushioning elements along the entire length of the cylindrical cavity. Chamfered, or otherwise tapered, caudal ends 12-1-2 of superior mandrel 12-1 wall segments 12-1-1 can create radial forces to keep central spring and/or cushion elements 5 centered within the cylinder as it moves up and down during normal spinal motions. Chamfered wall end shapes 12-1-2 can conform to cavity spaces provided by 3-1-3, which can permit wall mandrel chamfered ends 12-1-2 to descend completely into that cavity at maximum compression of cylinder 6-1.

Superior and inferior mandrels can have a plurality of cylindrical wall segments each of different arc degrees wherein the sum total of all the arc degrees is equal or less than 360 degrees and no wall of one interferes with a wall of the other during piston motion. In one embodiment, each wall-segment of a superior and inferior mandrel can be an approximately 60 degree section of a cylindrical shape, resulting in three wall-segments apiece. Interlacing these wall-segments allows them to slide past each other parallel to piston axis 21 and yet establish a single columnar support for spring/cushion elements within the cylinder cavity 6-1-4. In an alternative embodiment, each wall-segment of the superior and inferior mandrel can be an approximately 45 degree section, such that each mandrel has two wall-segments. While the 60 and 45 degree wall segments are described herein, it will be understood by a person skilled in the art that there could be any number of possible ways to divide the mandrel column into interlacing superior and inferior interlacing wall segments using segments of different angular dimension. Such variations are contemplated to be within the scope of the subject invention.

As mentioned previously, in the embodiments disclosed herein, the joint elements remain moveably attached to one another by means of a kinematic chain throughout nominal FSU workspace motion regardless of the orientation of the FSU in a force field, such as, for example, gravity. Therefore, they maintain the structural integrity of the arthroplasty in all FSU spatial configurations.

In a further embodiment, superior and inferior plates can be rigidly fixed to the superior and inferior vertebrae of a Functional Spinal Unit (FSU). In alternative embodiments, superior and inferior plates can be modified to easily attach or detach to other plates fixedly attached to the vertebra. An example of this is provided in U.S. Pat. Nos. 7,361,192 and 7,799,080, which are hereby incorporated by reference herein in their entireties, including any figures, tables or drawings. These references describe embodiments of a modular disc mechanism that can connect with a superior and an inferior plate by twisting or screwing into the superior and inferior plates, which can further be connected to the respective vertebra. The patents further describe a superior and an inferior plate that possess an opposite screw sense, such that twisting or turning in a single direction connects the modular prosthetic disc mechanism to both plates simultaneously. This can enable easier implantation and replacement of the prosthetic device, if necessary.

In one embodiment, central guide pins are fixedly attached to the superior and/or inferior plates. In a further embodiment, a plurality of peripheral guide pins are fixedly attached to the superior and/or inferior plates. In a more specific embodiment, one or more smooth central guide pins can also be fixedly attached to the superior and inferior plates and surrounded by a plurality of peripheral guide pins with barbs (FIG. 23), as illustrated herein, or with fusion spikes as described in U.S. patent application Ser. No. 13/157,539 (Doty) filed Jun. 10, 2011. Central guide pins can be longer than the barbed peripheral guide pins and/or fusion spikes, and can be partially inserted into pilot holes drilled into the vertebral interface surface before barbed guide pins or fusion spikes engage the cancellous bone. In a particular embodiment, at least one guide pin is used on each of the plates, and pilot holes are drilled into the inferior and superior vertebral interface surfaces before the barbed peripheral guide pins and/or fusion spikes engage the cancellous bone. In an alternative embodiment, more than one guide pin can be used. In a particular embodiment, at least one guide pin is used, centered on the inferior plate and one on the superior plate. The guide pins enable stable insertion and accurate placement of the device into the disc space of an FSU and can make an isotropic device workspace volume available to the FSU. Generation of anisotropic workspace volumes can be achieved by creating different joint stop limits for the various joints in possible conjunction with drilling the pilot holes for guide pins at points other than the vertebrae centroids. Implantation of devices with anisotropic workspace can be sensitive to orientation about the device's central axis 20 in neutral (refer to FIG. 7B) and should be taken into account. Guide pins can have indents, channels, and other surface treatments, the same as, or similar to, fusion spikes, to encourage bone fusion to the pin.

In one embodiment, a boot affixes to and between the superior and inferior plates. In a more particular embodiment, a protective, fluids/gases impervious, tough, flexible, fiber-reinforced boot fixedly attaches to and between the superior and inferior plates. The boot can be designed to be under slight tension in the FSU's neutral position and, thus, oppose increasing extension of the cylinder prismatic joint and can work antagonistically with spring/cushion elements in the cylinder cavity until the latter reach maximum decompression. Boot tension also can resist torsion loads on the device. In one embodiment, the boot utilizes a diamond weave fiber matrix, as instructed herein, or by weaving tough diagonal fibers within the boot as instructed in Doty in U.S. Pat. Nos. 7,361,192 and 7,799,080, and U.S. Published Application Nos. 2010/0070033 and US2010/0324688A1, and international published application no. PCT/US2010/37721, which are hereby incorporated by reference in their entireties, including any figures, tables or drawings.

In a further embodiment, a spring, cushion, and/or other types of compression resistant elements within cylinder 6-1 can oppose compression of the vertebral bodies of an FSU during normal operation due to changing cranial and muscular loading. Boot 17-1 and cushion elements 5-3 and 5-4 can be connected in such a manner as to act against extension and oppose compression under normal loads, regardless of rotation angle. In the neutral position, spring/cushion elements 5 can all balance boot and cranial load to produce a normal intervertebral separation. In those cases where boot elements are not used, the spring/cushion elements 5 can be designed to compress to a height equal to natural disc spacing under nominal load in neutral. With further loading, the spring and/or cushion elements can compress further until cylinder inferior surface 6-1-12 (FIG. 15) encounters superior surface 3-1-5 of ball-platform 3-1 (FIG. 7A). At that point, the body of the device can be completely compressed and becomes extremely rigid, transmitting all further load forces directly through the prosthetic body.

Rotation cushion 2-1 (FIG. 12) comprises, in one embodiment, a toroidal elastic tube that can be solid or hollow. The latter can be filled with compressible or non-compressible fluids/gases/gels. In a further embodiment, the rotation cushion lies on the bottom of inferior cavity 1-1-11 of inferior plate 1-1, surrounding minor socket 1-1-1 (FIG. 9), and below ball platform 3-1 (FIG. 13). As the superior plate 14-1 rotates with respect to inferior plate 1-1, ball platform 3-1 and ball 7-1 can accommodate the rotation motion and can rotate within the minor socket (1-1-1) and major socket (formed by inner spherical surface 1-1-2) within inferior cavity 1-1-11. As the ball platform 3-1 rotates, it can encounter and partially compresses rotation cushion 2-1, which tends to oppose further rotation. This action performs an important function provided by a natural disc, namely, resisting torsion. With this embodiment, energy is dissipated as the rotation cushion compresses on one side and expands on the opposite side of the tilting ball platform for any rotation, except along the polar axis of ball 7-1. The higher the durometer rating of the rotation cushion tube and the properties of elements that fill a hollow version, the greater can be the moment-of-force acting on the superior vertebra that is required to compress the rotation cushion.

In one embodiment, where a boot is employed, there is a compressible or non-compressible bio-compatible fluid, within the central cylinder, in conjunction with central spring/cushion elements, which can provide shock absorbing characteristics in addition to the static resistance to compressive loads along the piston axis 21 (see U.S. Patent Application Nos. US20100070033, PCT/US2010/37721, and US2010/0324688A1). In a further embodiment, the bio-compatible fluid can have a high viscosity.

In a further embodiment, the boot can be sealed, such that surrounding bodily fluids cannot contact the functional elements of the prosthetic device. In a still further embodiment, a sealed boot can seal in fluids to lubricate the functional elements of the prosthetic device. The piston prismatic joint can further act as a hydraulic pump, to help divert compression shocks to the walls of the boot, causing the boot to bulge or otherwise distort in shape and absorb some of the energy of the shock (see U.S. Pat. Nos. 7,361,192; 7,799,080 and U.S. Patent Application Nos. 20100070033, PCT/US2010/37721, and 2010/0324688A1). Fluid reservoirs can exist in the various cavities of the device. In one embodiment, the available space within the ball-piston space at maximum compression can be used as a fluid reservoir. Various hydraulic circuits can also be devised for the subject invention by one skilled in the art and such variations are considered to be within the scope of this invention.

The complete motion generality of the embodiments of the subject invention makes it applicable to any of a variety of situations. Advantageously, the complete three dimensional motion capability can track natural spinal FSU motion trajectories during simultaneous, dynamically changing, curvilinear, axial, lateral and sagittal rotations and translations, regardless of the details of that motion.

The device can also assist in accommodating variable disc spacing under static and dynamic load during normal FSU operation. For example, the disc spacing under static load in the neutral spinal position can be selected by adjusting parameters of spring and cushion elements within the device. The devices of the invention can absorb compression shocks, sustain static loads, and respond to dynamic loads. When implanted within a spine, the devices can also assist in alleviating spinal cord and nerve root compression. Certain embodiments also utilize a tough, flexible boot to resist torsion and extension forces. Other embodiments utilize a second boot covering that prevents the transfer of fluids and/or gasses. In alternative embodiments, these two functions are realized by a single boot covering that performs both functions.

The mechanism's components, when coupled together, forms a device that preserves its own mechanical integrity, connectedness (i.e., inseparable kinematic chain), and motion properties throughout the biologically constrained motion space (i.e., the workspace) of an FSU. The device can also allow for modification of the range of motion parameters and workspace, physical size, material composition, and mechanical strength to suit various mechanical applications, as well as spinal disc prosthetics applications.

When utilized as a spinal prosthetic, the complete 6-DOF motion capability of the prosthetic disc linkage mechanism allows natural FSU motions dictated by the muscles and ligaments of the spine. Advantageously, throughout nominal motion, the systems of the subject invention are capable of stabilizing an FSU because of their ability to maintain continuity of mechanical connection between a superior and inferior vertebrae, regardless of FSU orientation in space, while at the same time providing load bearing and permitting motion only within the nominal disc operating range or workspace. Mechanical continuity is realized by a kinematic chain of inseparable jointed elements.

An FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{nd}$ Addition, 1997). However, these angle limits do not reveal the underlying complexity of motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474, demonstrates this complexity in the cervical spine, even when the motion is restricted to flexion and extension.

The devices of the subject invention are able to accommodate a broader range of motions than other designs in a distinguished way. When utilized in a spine, the devices of the subject invention maintain disc stability, intervertebral spacing, and integrity under static and dynamic loads.

BRIEF DESCRIPTION OF DRAWINGS

In order that a more precise understanding of the above recited embodiments of the invention can be obtained, a more particular description of the invention will be rendered by reference to specific embodiments thereof that are illustrated in the appended drawings. The drawings presented herein may not be drawn to scale and any reference to, or implication of, dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

The central and peripheral guide pins can have chamfered (16-1-2, 15-1-2), or otherwise shaped tips, and smooth (16-1-1) or textured sides with possible barbs (15-1-1) on the peripheral pins.

Figure 2:
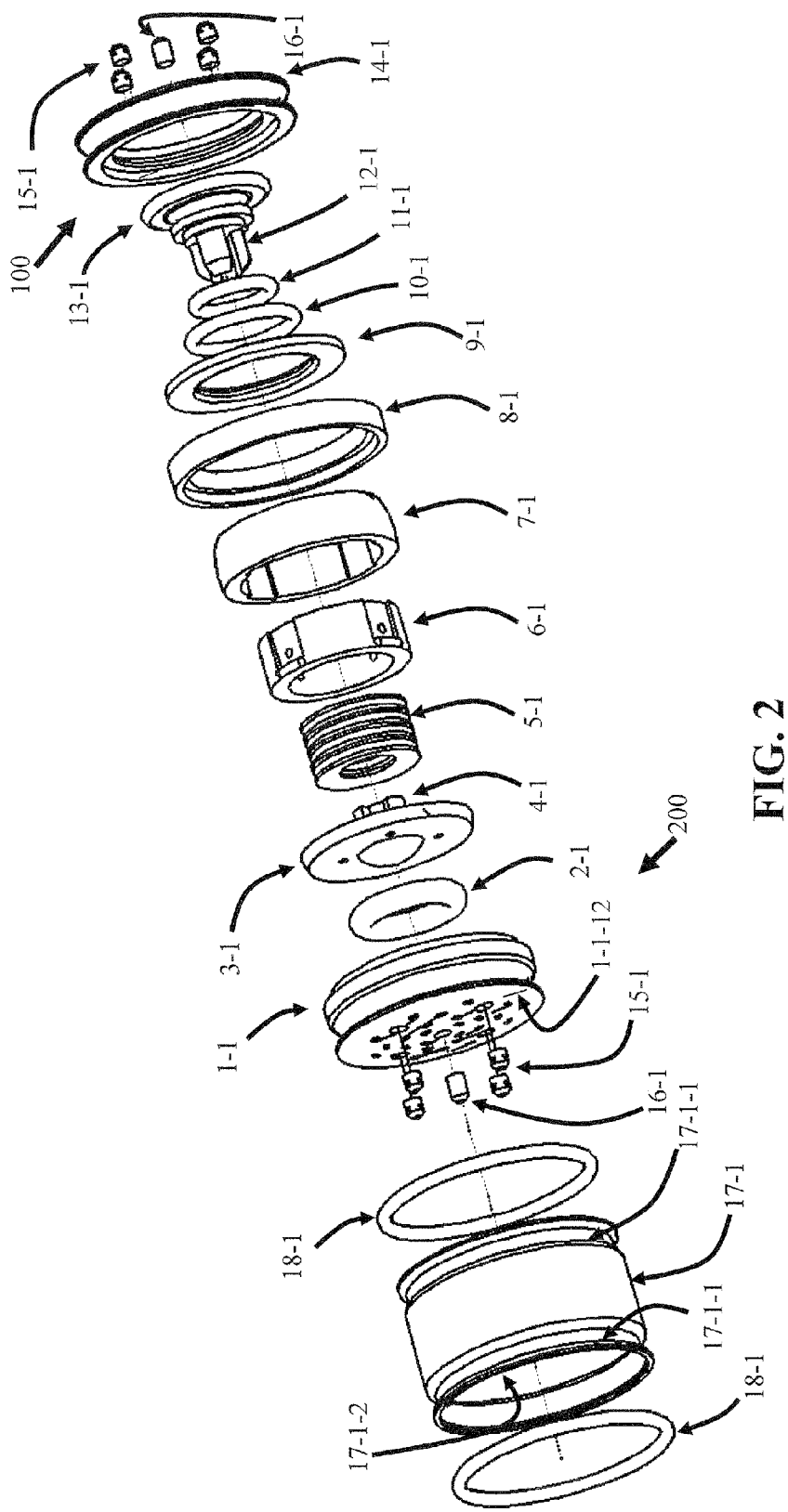

FIG. 2 illustrates the elements of a particular embodiment of the subject invention in an exploded perspective view. In this embodiment, a cylindrical shell-like boot 17-1 utilizing a tough, flexible, multi-layered, resilient, fiber-reinforced elastomer matrix can be firmly attached to superior and inferior plates (14-1 and 1-1) with clamping rings/bands 18-1. The cylindrical elastomer boot 17-1 embodiment envelops the rest of the components in this embodiment of the subject invention within cavity 17-1-2, with the exception of the upper and lower surfaces of the superior and inferior plates and guide pins 15-1 and 16-1. Grooves 17-1-1 at the superior and inferior ends of the boot allow clamping rings/bands 18-1 to firmly fix the boot to superior and inferior plates 14-1 and 1-1. The boot grooves can be tougher and less flexible than the rest of the boot. In a further embodiment, an adhesive sealant can be applied to the top and bottom edges of the boot before clamping to help create a seal that retains fluids and/or gases within the boot cavity 17-1-2 as well as blocking fluids or gases out of the boot cavity. In one embodiment, the anterior wall of the boot can stretch about 8-10% more than the posterior wall of the boot, so the former is more elastic than the latter. The boot can typically stretch 20% from neutral to full extension. The left lateral and right lateral "sides" of the boot can also be stiffer than the posterior and anterior "sides" to resist lateral rotations and translations.

Guide pins 15-1 and central guide pin 16-1 can be fixedly attached to superior and inferior plates 14-1 and 1-1 by means of pin cavities 14-1-7, 14-1-8, 1-1-7, and 1-1-8, respectively (see FIG. 3 and FIG. 17) or can be integrally manufactured as part of the plates. The guide pins can insert into cancellous bone via pre-drilled pilot holes. In an alternative embodiment (FIG. 17), central and peripheral guide pins further help to secure the superior and inferior plates into the superior and inferior vertebrae of an FSU by allowing bone ingrowths in micro-fissures and tunnels (15-2-1).

In this embodiment, toroidal cushion element 2-1 serves to resist rotations of the superior plate 14-1 relative to the inferior plate 1-1 about any axis passing through center of curvature 22 and perpendicular to axis 21 of piston 25 (FIG. 7). Ball platform 3-1 supports spherical segment shell 7-1 with a cylindrical cavity called the "ball", at all times, but only supports the piston cylinder 6-1 at full compression. Spring/cushion elements 5 (FIG. 25) also rest on the ball platform.

Figure 20:
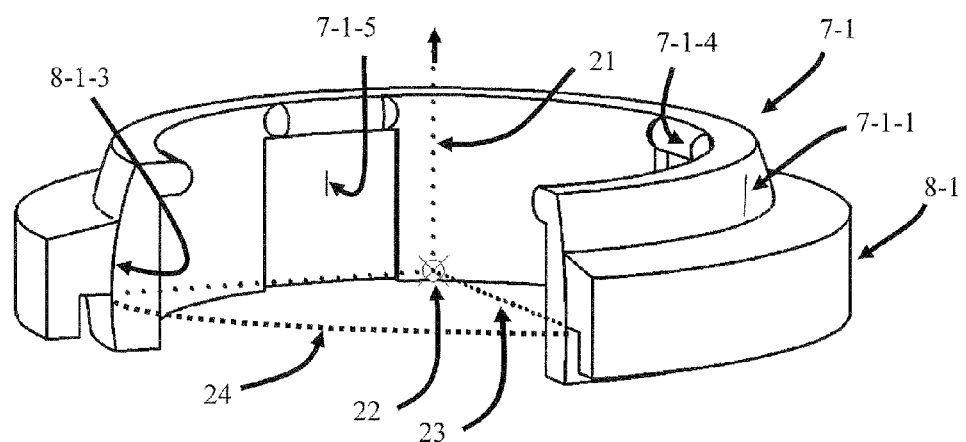

Ball retainer 8-1, of this embodiment, has a spherical inner surface with the same center of curvature 22 and radius of curvature 23 as the exterior spherical surface of ball 7-1 (FIG. 20). The ball includes the equator 24 of the defining spherical segment shell as does edge 8-1-4 of the ball retainer 8-1. Ball retainer 8-1 can slide down over the superior surface of ball 7-1 from above, but cannot descend past the equator of the ball. When elements 2-1, 3-1, 4-1, 5-1, 6-1, and 7-1 of this embodiment are appropriately stack assembled into a cavity within inferior plate 1-1, and the ball retainer 8-1 is fixedly attached to 1-1, all those elements can form a kinematic linkage with lower order joint pairs consisting of a ball-and-socket and an axial prismatic joint, and will not separate under normal operation.

Figure 8:
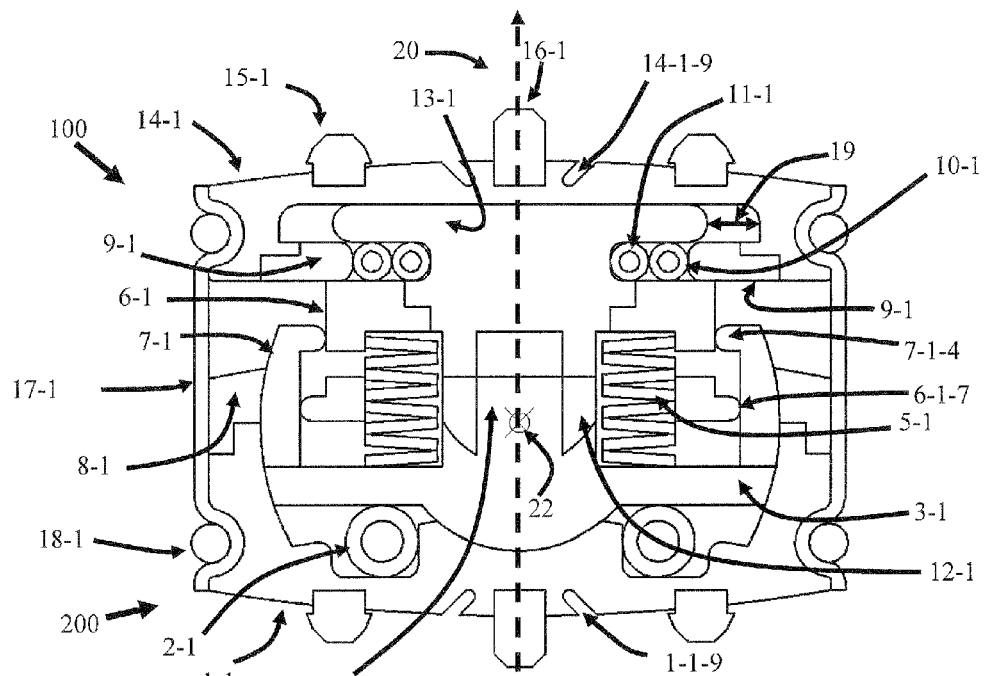

In this embodiment, the piston head 13-1 and superior mandrel 12-1 can be an integrated element. Planar cushion elements 10-1 and 11-1 fit into a bearing raceway of the piston head 13-1 (FIG. 8). Elements 13-1, 10-1, and 11-1, and 12-1 (piston head, cushion element, and superior mandrel, respectively) become inseparable from superior plate 14-1 by planar retainer 9-1. When the piston shoulder 13-1-4 is press fit or otherwise fixedly attached to piston cylinder 6-1, configured in the subassembly described in the previous paragraph, the entire device becomes inseparable, but operably connected. A more detailed description of device assembly is discussed later.

Figure 3:
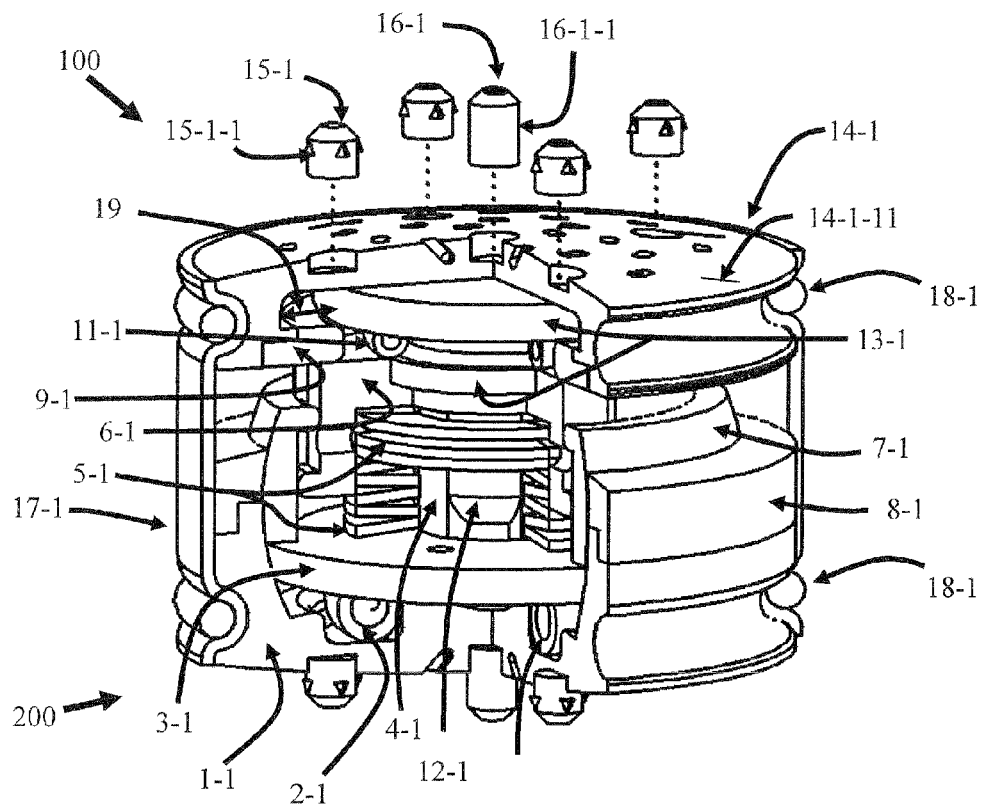

FIG. 3 illustrates a perspective, quadrant-cutaway view of an assembled, particular embodiment of the invention when employed as a spinal disc prosthesis. This view represents a configuration obtained when the spinal vertebrae, which it connects to, are in neutral position. Superior plate 14-1 fixedly attaches to a superior vertebra of an FSU and inferior plate 1-1 fixedly attaches to the inferior vertebra of that same FSU. Ball platform 3-1 engages rotation cushion 2-1 resting below it in inferior cavity 1-1-11 only as it rotates. Spring/cushion elements 5 (FIG. 25) are partially compressed due to cranial and other load factors. Multi-walled superior mandrel 12-1 and multi-walled inferior mandrel 4-1 are partially engaged and can slide by one another in alternating wall segments. In a particular embodiment, with mandrel elements, there is a choice of spring/cushion elements 5-1, 5-2, 5-3, or 5-5. In another particular embodiment, both mandrel elements and all the spring elements can be replaced entirely by an elastic, thermoplastic cylinder 5-4 without a cylindrical hole. Planar retainer 9-1 retains piston head 13-1 within cavity 14-1-2 of superior plate 14-1. When 13-1 press fits into, or is otherwise fixedly attached to, piston cylinder 6-1, then it mechanically, but operationally, links or connects cylinder 6-1 and superior plate 14-1 together. Ball element 7-1 limits the extension stroke of the piston by means of first and second bearing interlocks 6-1-7 and 7-1-4, respectively, and the ball platform 3-1 limits the compression stroke of the piston by interfering with 6-1. A spherical socket within 1-1 (refer to FIG. 9) along with ball retainer 8-1 encapsulate the spherical segment shell (ball element) 7-1, preventing its withdrawal from the socket. In this particular embodiment, one can see the kinematic linkage of all the lower order pairs within the device, from the superior plate 14-1 to the inferior plate 1-1.

Figure 4:
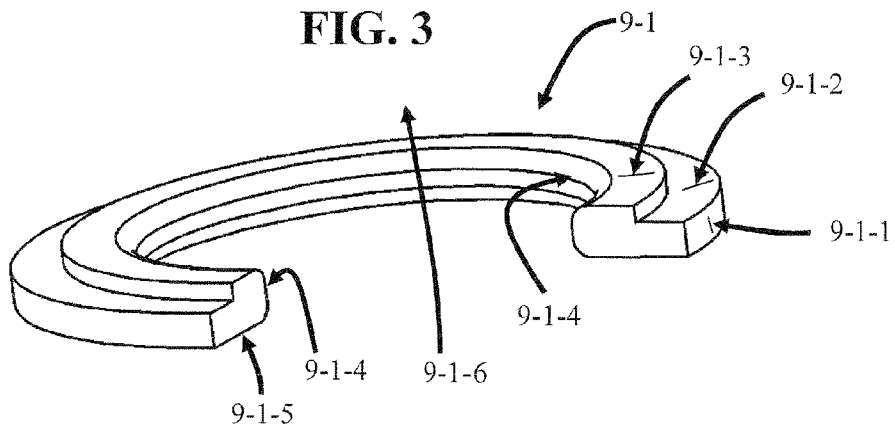

FIG. 4 shows planar retainer 9-1. Lateral surface 9-1-1 and retainer upper surface 9-1-2 press fit into, or otherwise fixedly attach within, a receptacle on the inferior portion of the superior plate 14-1. Retainer curvate surface 9-1-4 encounters planar cushions during motion of the superior plate with respect to the piston head 13-1. Central retainer hole 9-1-6 is too small for piston head 13-1 to be extracted from cavity 14-1-2 of the superior plate 14-1, once retainer 9-1 is installed. Slider surface 9-1-3 slides planarly along the superior surface of bearing raceway 13-1-3. Planar retainer lower surface 9-1-5 slides planarly along cylinder planar surface 6-1-5.

Figures 5A, 5B:
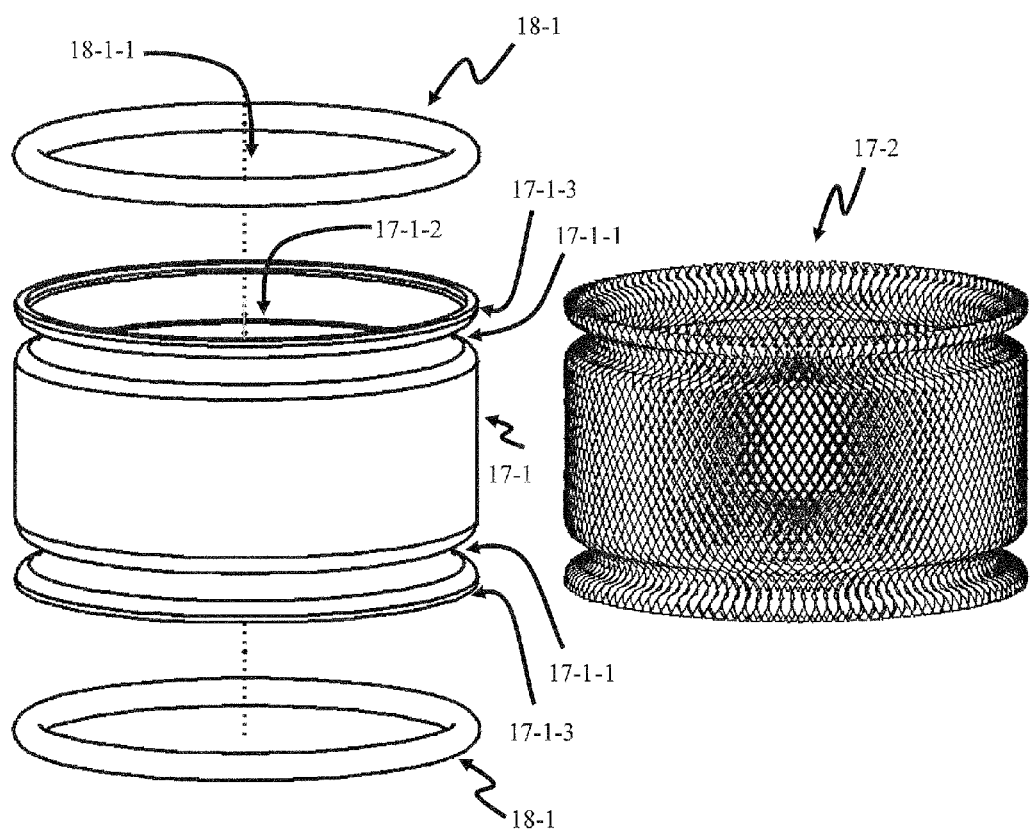

FIG. 5A illustrates boot 17-1 and boot retainer rings 18-1 while FIG. 5B depicts a fiber boot 17-2 with a diamond weave. The fiber boot can be separate from boot 17-1, in which case the boot 17-1 can be much thinner and more flexible and serve as a covering of fiber boot 17-2 as well. In another embodiment, the diamond fiber woven boot 17-2 is embedded and integrated into a flexible, durable elastomer boot 17-1.

FIG. 6 A, B, and C show perspective elevation views of a particular embodiment in full flexion (FIG. 6A), neutral (FIG. 6B), and full extension (FIG. 6C) when employed as a spinal disc prosthesis.

FIG. 7 A, B, and C show a sagittal plane section of a particular embodiment in full flexion (FIG. 7A), neutral (FIG. 7B), and full extension (FIG. 7C), when employed as a spinal disc prosthesis. In full flexion, spring/cushion elements 5 and rotation cushion 2-1 are maximally compressed. In full extension, spring/cushion elements 5 are minimally compressed and rotation cushion 2-1 is maximally compressed again. In one embodiment with completely symmetrical joint stops, FIG. 6 and FIG. 7 can be an elevated and cross sectional view, respectively, with respect to any plane passing through the device's central axis 20, said axis being coincident with piston axis 21 when the device is in its neutral configuration (FIG. 7A, B, and C).

FIG. 8 depicts a sagittal plane section of the device as in FIG. 7B, but with two planar cushions 10-1 and 11-1 and sections of the boot 17-1 and boot retainer elements 18-1. In general, a plurality of planar cushions of various shapes and sizes can be used. Angular curvate slots (bone fusion cavities) 14-1-9 on superior plate 14-1 and 1-1-9 on inferior plate 1-1, allow for bone growth into those plates for further securing the device within a Functional Spinal Unit (FSU). In one embodiment, the bone fusion cavities are drilled into the surface of the inferior plate at an angle that is less than 90° relative to the inferior surface 1-1-12.

Figure 9:
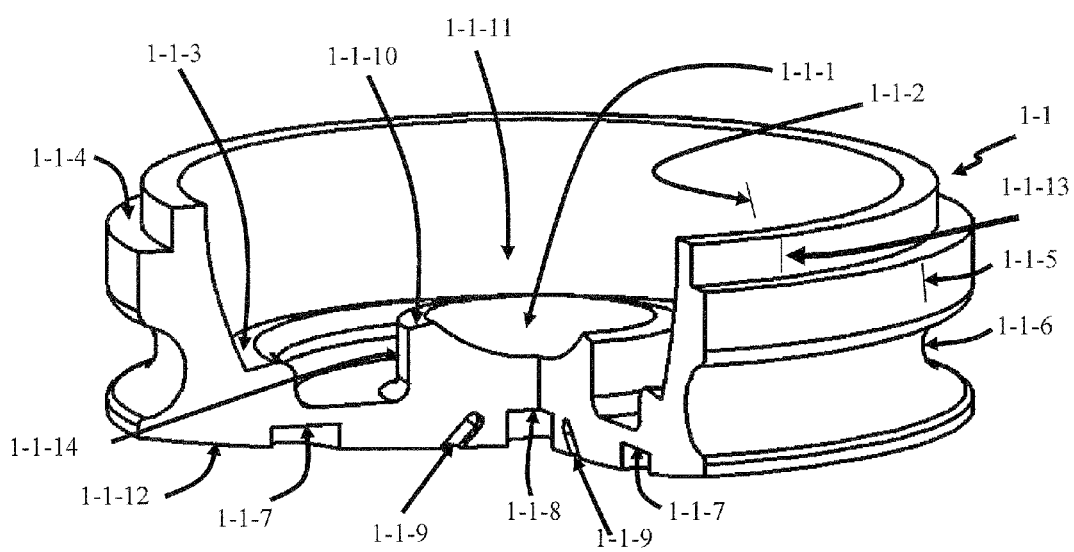

FIG. 9 shows a perspective, quadrant-cutaway view of an embodiment of a superior plate 1-1, according to the subject invention. This element provides a double spherical socket for ball platform 3-1, namely, spherical surfaces that form minor socket 1-1-1 and the inner surface of the lower portion of ball cavity 1-1-2. Both these spherical surfaces can have the same center of curvature 22 as can the spherical surfaces 3-1-4 on the ball platform, the inner spherical surface 8-1-3 (FIG. 18) of ball retainer 8-1, the outer spherical surface 7-1-1 of ball 7-1 (FIG. 19), and spherical segment 3-1-1 of ball platform 3-1. Spherical surfaces 1-1-2, 3-1-4, 7-1-1, and 8-1-3 can have the same radius of curvature 23. Spherical segment 3-1-1 can fit into socket 1-1-1. As the ball platform rotates within socket 1-1-1, outer ledge 1-1-3 and central ledge 1-1-10 function together as a general rotation joint stop. Both ledges can have the same inclination and, together, can limit, by means of kinematic linkage, rotations of superior plate 14-1 for any rotations about an axis passing through center of curvature 22 and perpendicular to 21. Lower recess 1-1-4 conforms to inferior surfaces 8-1-4 and 8-15 of ball retainer 8-1 and allows press fitting, or otherwise fixedly attaching, ball retainer 8-1 to inferior plate 1-1. Inner spherical surface 8-1-3 can smoothly continue inner spherical surface 1-1-2 of inferior cavity 1-1-11 when 8-1-3 is so affixed to 1-1. Groove 1-1-6 in a particular embodiment allows firm clamping of boot 17-1 to 1-1.

Figure 10:
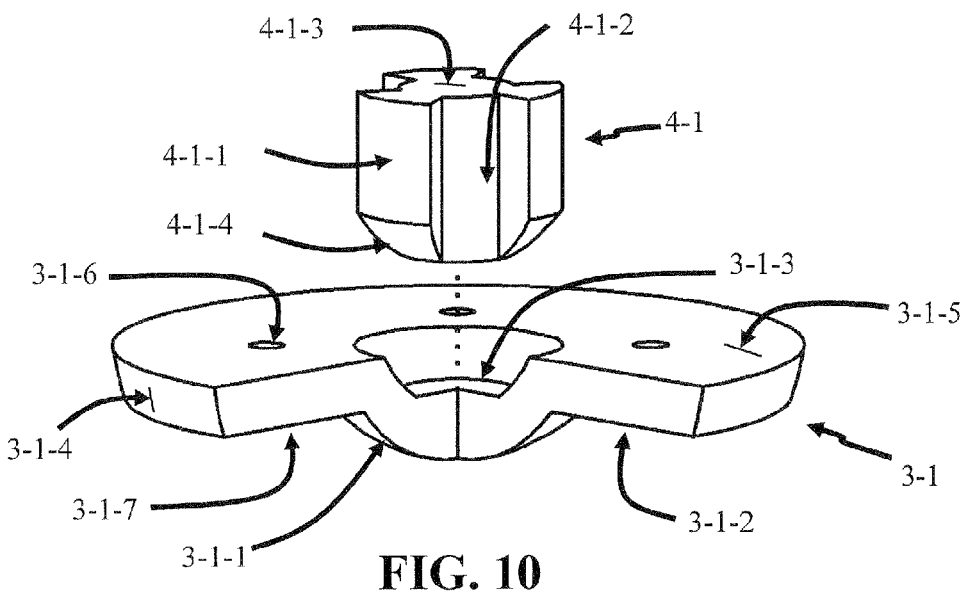
Figure 13:
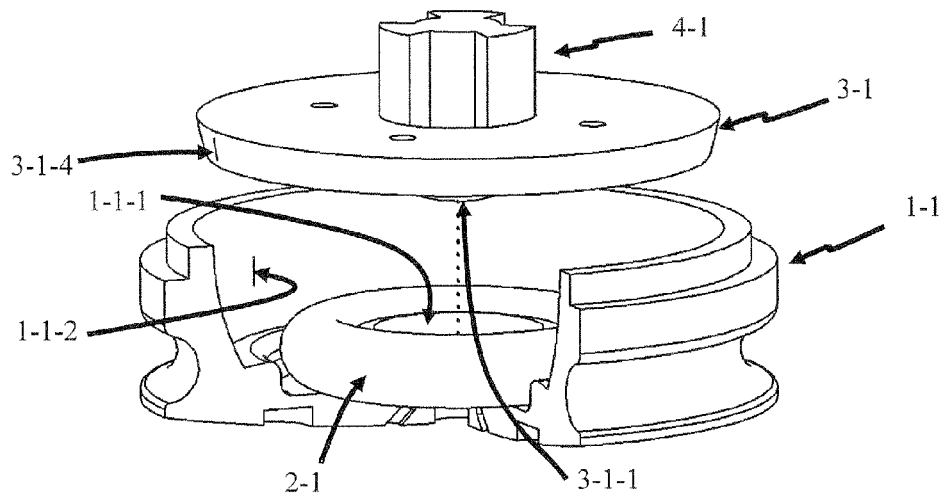

FIG. 10 illustrates an embodiment of the ball platform 3-1 and inferior mandrel 4-1 of the subject invention in perspective, slightly tilted forward in the plane of the page. In FIG. 10, the segmented-wall, inferior mandrel 4-1 is illustrated as a separate part from the ball platform, which can be fixedly attached to realize the configuration in. FIG. 13. In this embodiment, the tapered wall segments of the superior mandrel 12-1 fit into conforming cavities 3-1-3-1 on the superior surface of the ball platform 3-1. In FIG. 7A, the penetration of 12-1 into these cavities can be seen in cross-section.

Figure 11:
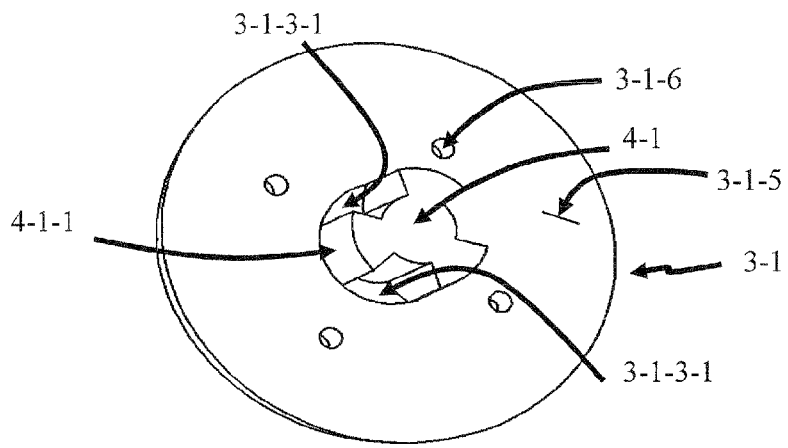

Alternatively, ball platform 3-1 and inferior mandrel 4-1, seen from above and at an angle in FIG. 11, can be manufactured as an integrated unit. In a specific embodiment, an inferior mandrel 4-1 has three wall segments 4-1-1 separated by three slots 4-1-2 into which wall segments of a superior mandrel slide. A central core 4-1-3 provides additional structural strength. Taper 4-1-4 may only be required if 4-1 is manufactured separately from 3-1. Slot cavities formed by inserting 4-1 into cavity 3-1-3 can be milled/cast/stamped out in an integrated manufactured version.

In this specific embodiment, shown in FIG. 10, spherical surface 3-1-4 can have radius of curvature 23 and the same center of curvature 22 as the spherical segment 3-1-1, which has a smaller radius of curvature. Center of curvature 22 can also be the rotation center of any rotation of the superior plate 14-1 with respect to the inferior plate 1-1. Ball lower surface 7-1-6 can contact ball platform surface 3-1-5 at all times and in a still further specific embodiment, those surfaces conform with each other. They can be fixedly attached to each other or not. In either case, after assembled with ball retainer 8-1 in place, ball 7-1, ball platform 3-1, and rotation cushion 2-1 can be confined to socket of 1-1 during all motions within the workspace of the FSU. Inferior surface 6-1-2 (FIG. 15) of cylinder 6-1 only contacts surface 3-1-5 at the extreme down stroke of the piston 25 (FIG. 16) (elements 6-1, 13-1, and 12-1 fixed together) and can conform to that surface. In a particular embodiment, all three surfaces are planar. A plurality of hydraulic portals 3-1-6 can allow the passage of biocompatible fluids/gases between the chamber below the ball platform and the chamber defined by ball 7-1 and piston 25 as the cylinder moves up and down within the ball.

Figure 12:
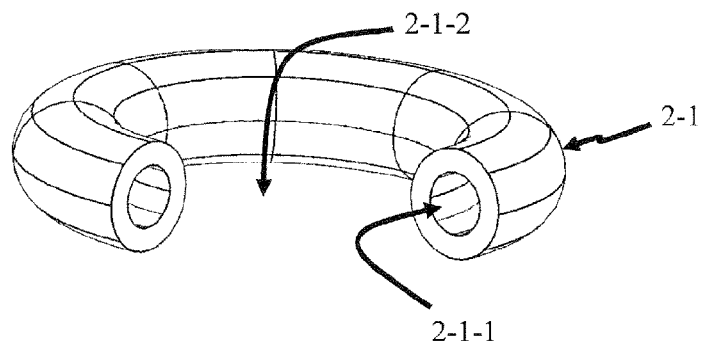

FIG. 12 illustrates a perspective quadrant-cutaway of an embodiment of a rotation cushion. This toroidal shaped element can be a soft, solid elastomer or artificial disc nucleus or comprise an elastic shell with an inner cavity 2-1-1 filled with biocompatible gas, fluid, or gel. In one embodiment, this cushion opposes rotations of ball platform 3-1 with compressive forces acting laterally on the side of the tube.

FIG. 13 shows a perspective view of an embodiment with insertion of the rotation cushion 2-1 and ball platform 3-1 into larger inferior cavity 1-1-11 of inferior plate 1-1 with a quadrant-cutaway to allow viewing. Rotation cushion 2-1 lies on the floor of the larger socket cavity and surrounds platform 1-1-14 with minor socket cavity 1-1-1 into which spherical segment 3-1-1 rotationally seats.

Figure 14:
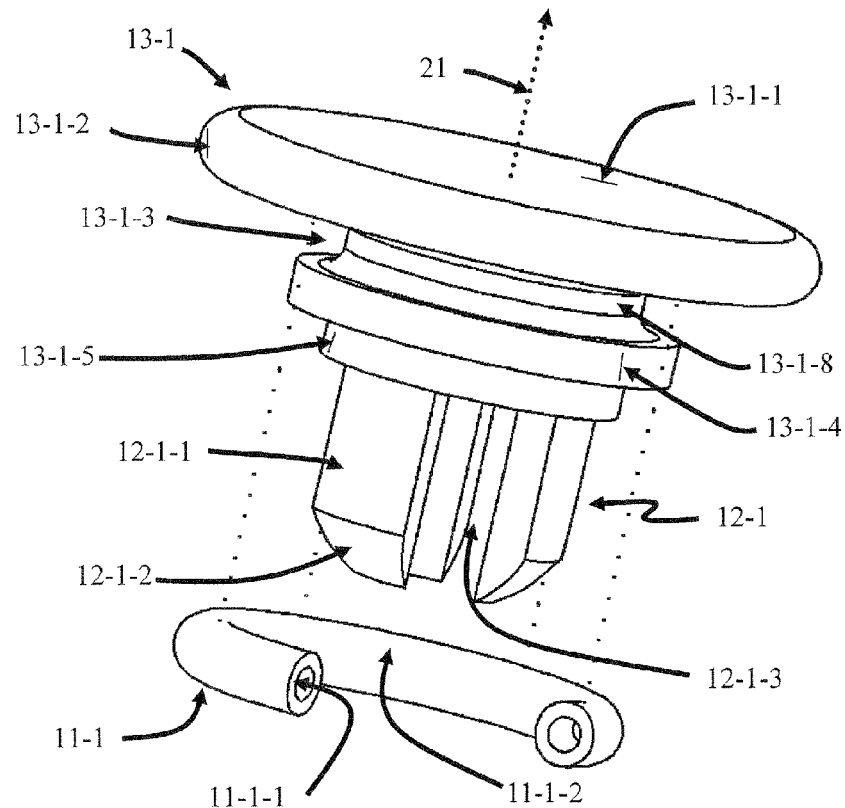

FIG. 14 depicts a perspective view of an embodiment of a segmented-wall superior mandrel 12-1 fixedly attached to, or manufactured as a single piece with, piston head 13-1. These two integrated elements, as a single unit, press fit, or are otherwise fixedly attached, into opening 6-1-9 of cylinder 6-1 to comprise a piston 25 (refer to FIG. 16). Piston 25, during normal operation, translates as a single unit parallel to axis 21. In a specific embodiment, the superior mandrel can have three wall segments 12-1-1 that slide within the three slots of the inferior mandrel 4-1-2. Wall tapers 12-1-2 conform to the taper of receiving cavities 3-1-3-1 of ball platform 3-1. The wall tapers 12-1-2 can establish a centering force on spring elements to keep them from jamming the piston stroke action. In some embodiments, superior mandrel 12-1 is eliminated.

Piston head 13-1 supports a piston planar surface 13-1-1 which comprises a principal surface of a planar pair joint. Superior plate planar surface 14-1-1 (FIG. 17) in the cavity of the superior plate comprises the other principal surface of the planar pair joint. Recess 14-1-4 allows press fit insertion of planar retainer 9-1 once the piston head is in place. Piston head "lip" surface 13-1-2 can be curvate. Piston shoulder element 13-1-4 and superior mandrel base 13-1-5 can press fit into a recess on top of cylinder 6-1. Bearing raceway 13-1-3 can accommodate a plurality of toroidal planar cushions, for example, 10-1 and 11-1, comprising smaller versions of rotation cushion 2-1.

Figure 15:
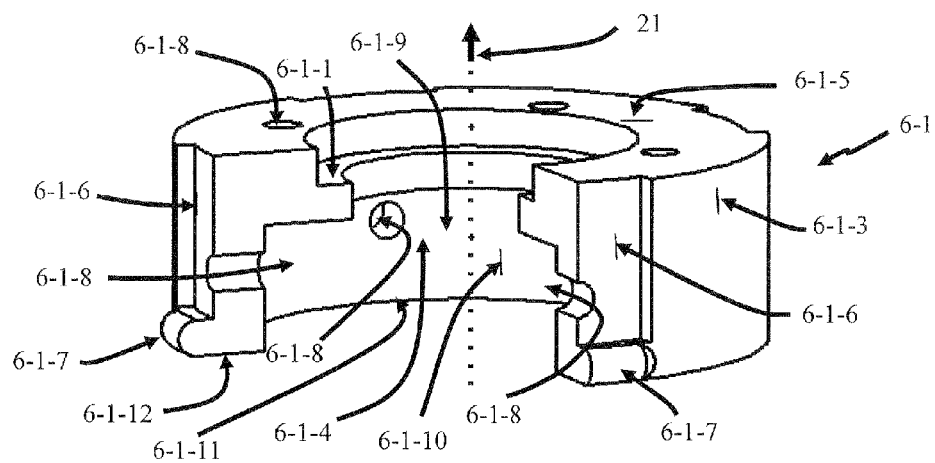

FIG. 15 shows a quadrant-cutaway view of an embodiment of cylinder 6-1 with lateral surface 6-1-3 and internal lateral surface 6-1-10, both of which can be cylindrical. Surface 6-1-3 can support a plurality of vertical bearing raceways 6-1-6, open at the cranial end and terminated by a first bearing interlock 6-1-7 at the caudal end. In the embodiment shown, there are four such raceways. Each raceway can support a plurality of hydraulic portals 6-1-8. One hydraulic port per raceway is shown in the diagram. Offset from these portal openings, there can be a plurality of hydraulic portals 6-1-8 on cylinder planar surface 6-1-5 at the top of the cylinder body, which surface supports planar retainer lower surface 9-1-5 during the relative motion between plane surfaces 13-1-1 and 14-1-1 of the planar pair. Cylinder inferior surface 6-1-2 can rest on ball platform surface 3-1-5 at maximum compression of spring/cushion elements, which fit into cylinder central cavity 6-1-4 at maximum compression. Cylinder opening 6-1-9 allows press fit insertion of piston shoulder 13-1-4 and superior mandrel base 13-1-5. Ledge 6-1-1 limits the insertion depth.

Figure 16:
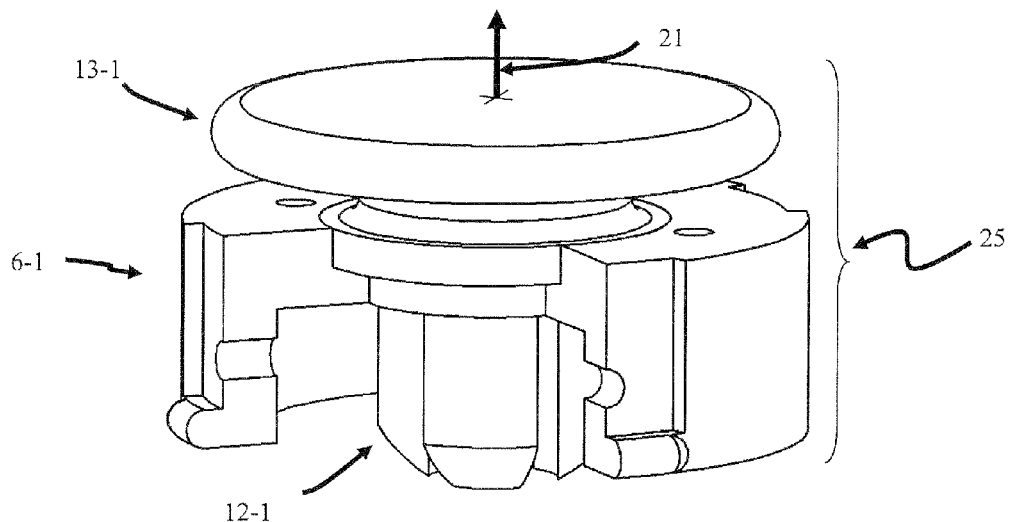

FIG. 16 illustrates a perspective, quadrant-cutaway view of one embodiment of piston 25, said piston comprising three principal elements, piston head 13-1, superior mandrel 12-1, and cylinder 6-1.

Figure 17:
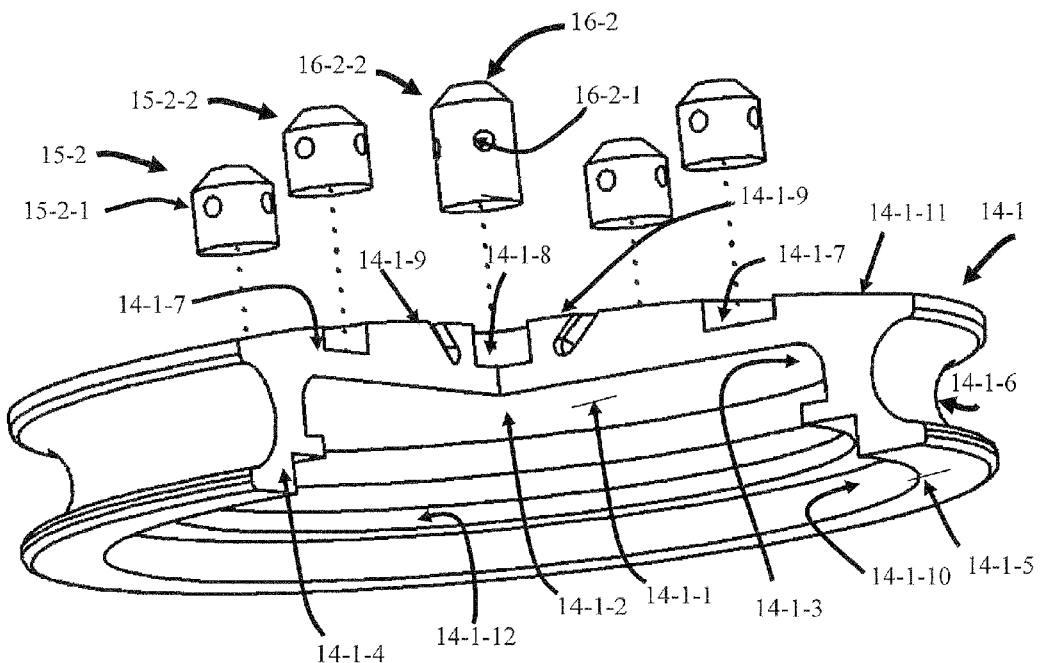

FIG. 17 shows an embodiment of a superior plate 14-1 from a tilted, slightly caudal perspective. In this embodiment, cavity 14-1-2 permits the insertion of the piston head 13-1, which is smaller than the cavity and can move about on planar surface 14-1-1. Planar retainer 9-1 (FIG. 4) can seat fixedly into superior plate recess 14-1-4 bounded by orifices 14-1-10 and 14-1-12 within planar socket cavity 14-1-2 of superior plate 14-1. The boundary surface 14-1-3 of the planar pair cavity can intersect with projection or lip 13-1-2 on the piston head 13-1 in a curvate line when the plate 14-1 slides to an extreme extent, that is, when lip 13-1-2 abuts the cavity wall surface 14-1-3. Cavity wall surface can have any of a variety of surface configurations, including but not limited to circular, rounded-corner square, elliptical, polygonal, curvate or other closed planar curve. It is preferable, though not required, for the shape of the lip 13-1-2 of the piston head to be complementary to the shape of the cavity wall surface 14-1-3. Surface 14-1-5 can slide along surface 6-1-5 during planar motion of 14-1 and 9-1 during operation of the planar pair joint. During all such motions, the planar retainer 9-1 maintains the integrity of the planar pair joint by preventing out-of-the-plane separation (within tolerances) of the sliding surfaces of the joint.

Convex curvate superior surface 14-1-11 can also support a plurality of pin cavities 14-1-7 for inserting the peripheral guide pins and a singular, centered pin cavity, 14-1-8 for inserting the central guide pin. In one embodiment, the pins are milled/cast/stamped as part of the superior plate 14-1; thus, the pin cavities 14-1-7 and 14-1-8 are not needed. A plurality of slanted, curved bone fusion cavities 14-1-9, milled in a variety of patterns, for example, random or spiral, allow for bone ingrowths to further secure the device to a superior vertebral body of an FSU. In a particular embodiment, each hole is milled by a bit slanted off normal and rotating about axis 20 for a small angle. Grooves 14-1-6 can provide a means for attaching boot 17-1 to superior plate 14-1. In one embodiment, the bone fusion cavities are drilled into the surface of the superior plate at an angle that is less than 90° relative to the superior surface 1-1-12.

FIG. 17 also depicts an alternative embodiment for guide pins 15-2 and 16-2, wherein fissures or indents 15-2-1 or 16-2-1 within the pins allow for bone ingrowth. As with other guide pins, the ends can be chamfered 15-2-2 and 16-2-2 or tapered to insure easy initial insertion of the superior and inferior plates 14-1 and 1-1.

Figure 18:
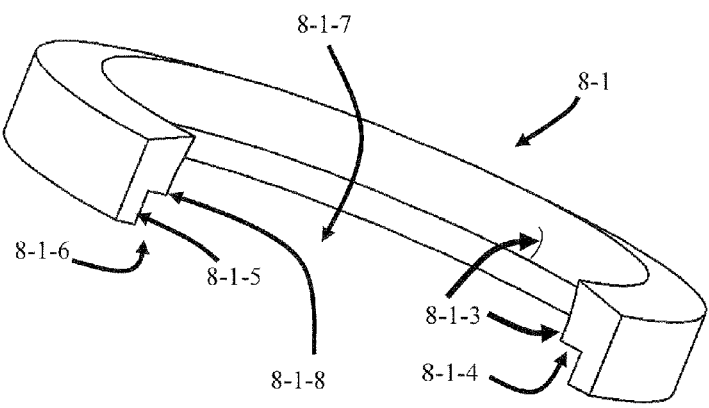

FIG. 18 depicts a perspective, quadrant-cutaway view of an embodiment of a ball retainer 8-1 as viewed when slightly tilted counterclockwise about the lateral axis and rotated counterclockwise about the sagittal axis. Spherical surface 8-1-3 can have the same radius 23 and center 22 of curvature as the ball surface 7-1. Interior edge 8-1-8 of lower inside surface 8-1-4 constitutes a great circle of a sphere whose radius of curvature 23 can equal that of the ball spherical surface radius 23. Orifice 8-1-7 can allow ball retainer 8-1 to slip over ball element 7-1 from the top until it rests on equator 24. This is shown in FIG. 20.

Figure 19:
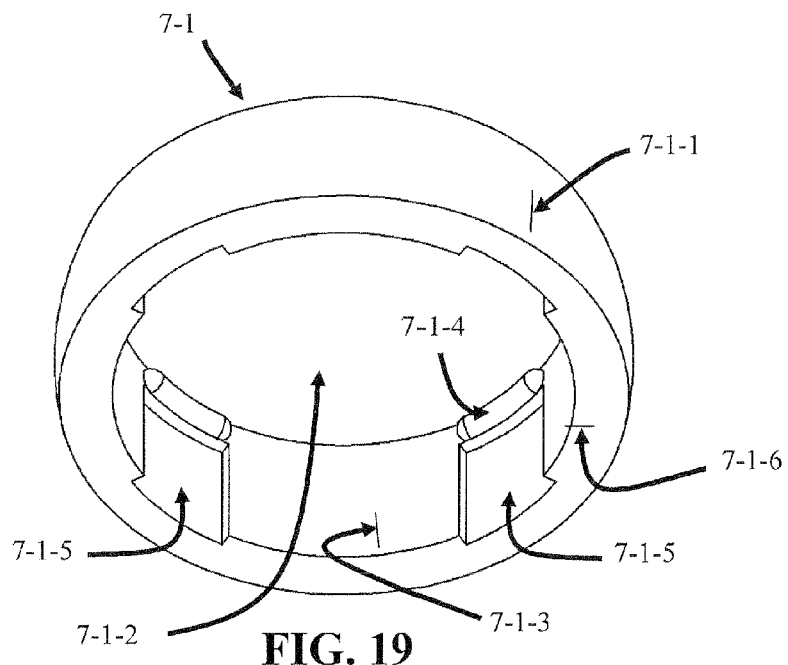

FIG. 19 shows a perspective view of a particular embodiment of spherical segment shell 7-1, also called the "ball" element, as seen from below and slightly tilted into the page. This shell segment embodiment encompasses at least one great circle of the defining sphere. One such great circle (FIG. 20) can be called the equator 24 of the ball. When assembled, the plane of the equator 24 of the great circle, in this embodiment, always parallels the planes of the piston planar surface 13-1-1 and the superior plate planar surface 14-1-1 of the planar pair joint. Rotation of the ball defines the rotation of superior plate 14-1 with respect to inferior plate 1-1. Outer spherical surface 7-1-1 can have the same ball radius 23 and center of curvature 22 as the inner spherical surface 1-1-2 of inferior plate major cavity 1-1-11. Raised, spherical socket cavity 1-1-1, also within major cavity 1-1-11 of the inferior plate 1-1, has a center of curvature 22, but a much smaller radius of curvature. Interior ball surface 7-1-3 can conform to exterior cylinder surface 6-1-3 to allow sliding action of the piston 25 within the ball cavity 7-1-2. A plurality (four in the diagram) of bearing raceways 7-1-5 match, in number and position, the plurality of bearing raceways 6-1-6 on the cylinder 6-1. Raceways 7-1-5 can open at the caudal end and can be closed at the cranial end by fixed bearing element 7-1-4. Cylinder 6-1, during assembly can slide up through ball cavity 7-1-2 without interference between it and the ball element 7-1, until first bearing interlock 6-1-7 engages second bearing interlock 7-1-4, at which point no further sliding along piston axis 21 is possible. The ball lower surface 7-1-6 can rest on the ball platform 3-1 and can be fixedly attached, or not, to same.

In perspective, quadrant-cutaway view of ball 7-1 and ball retainer 8-1 of FIG. 20, the circle equator 24 is a great circle of a sphere with center of curvature 22 and radius of curvature 23. Outer spherical surfaces 7-1-1 and the spherical surface of the ball retainer 8-1-3 can have this same radius and center of curvature. Lower inside edge 8-1-8 of lower inside surface 8-1-4 can also be a great circle with center and radius of curvature 22 and 23, respectively, when appropriately placed down over the ball. Ball retainer 8-1 can slip over the top of ball 7-1, and when the great circles coincide in 24, ball retainer 8-1 can no longer continue to slide downward, because edge 8-1-8 abuts the outer spherical surface equator 24. When lower recess 1-1-4 of inferior plate 1-1 press fits into, or fixedly attaches to, recess 8-1-4, ball retainer 8-1 prevents ball 7-1 from being extracted from inferior plate major cavity 1-1-11, this without interfering with the three independent degrees of rotational freedom of operation of the ball within that cavity.

Figure 21:
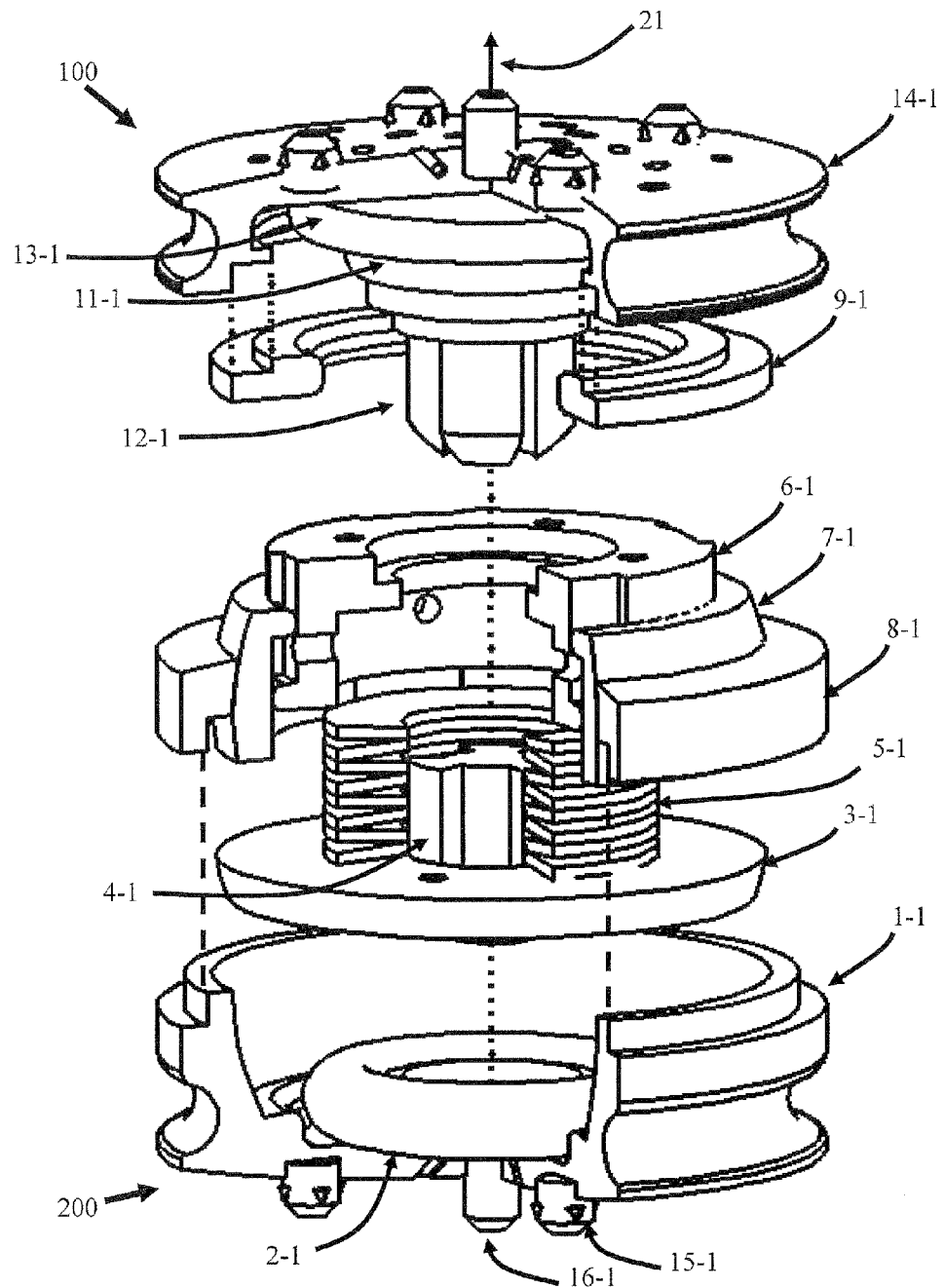

FIG. 21 shows how an embodiment of the device can be assembled by stack assembling a lower and an upper subassembly, then stack assembling the two subassemblies. The following description assumes that the superior and inferior plates 14-1 and 1-1 and guide pins 15-1 (15-2) and 16-1 (16-2) have already been assembled or milled/cast/stamped from a single piece.

FIG. 22 illustrates embodiments of Belleville springs that can be utilized with certain embodiments of the subject invention. A plurality of Belleville springs can be series or parallel stacked with each spring having a possibly different stiffness. FIG. 22A shows an embodiment with 10 Belleville springs stacked in series. Belleville springs 5-1 can be employed as a spring element to resist compression strokes of the piston 25. In FIG. 22B a perspective, quadrant-cutaway view of a Belleville spring can be seen. A more complete discussion of Belleville springs and their usage appears in U.S. Pat. No. 7,927,375 and U.S. Patent Application 2010/0324688, which are hereby incorporated by reference in their entirety, including any tables, figures or drawings.

FIGS. 23A and B illustrate embodiments of guide pins 15-1 that have a plurality of barbs 15-1-1 and embodiments of a central guide pin 16-1-1 (FIG. 23B) having a smooth barrel. These guide pins can be press fit or bonded into pin cavities 14-1-7 and 14-1-8, respectively, or milled/cast/stamped as an integral part of the superior and inferior plates 14-1 and 1-1. A central guide pin can have a smooth cylindrical surface 16-1-1 for easy insertion into cancellous bone. Peripheral guide pins and central guide pins can have chamfers 15-1-2 (15-2-2) and 16-1-2 (16-2-2), respectively, or other tapered or pointed shapes to establish easy initial insertion into pre-drilled holes. Hole tolerance for central guide pins 16-1 (16-2) can be relaxed in this embodiment to make for smooth easy insertion of the central pins. Since the central pin is longer than the peripheral pins, during implantation of the device in an FSU, it can be positioned and partially inserted before the peripheral pins make contact with the bone. The device can then be slightly rotated about the partially inserted central pins until the peripheral guide pin pilot holes line up with the peripheral guide pins. Insertion can then be completed. The peripheral guide pin pilot holes can be approximately the diameter of the cylinder portion of 15-1, allowing the barbs on the peripheral guide pins to bite into the cancellous bone to help fix superior plate 14-1 and inferior plate 1-1 firmly to the FSU vertebrae at implantation time.

Figure 24:
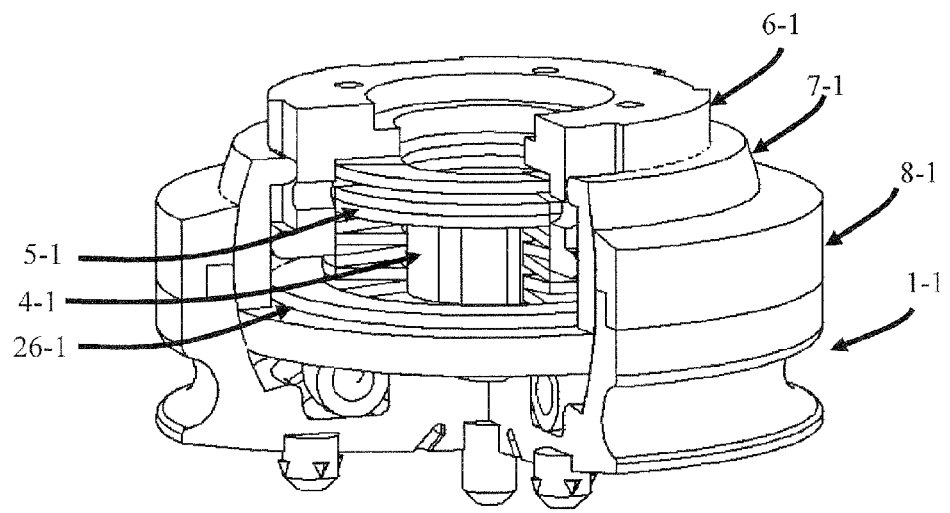

FIG. 24 illustrates a compressible, elastomer washer cushion 26-1. A washer cushion reduces the amount of downward stroke of the piston 25 (FIG. 16) and compresses to shock absorb any impact on the ball platform 3-1 due to excessive compression.

Figure 25:
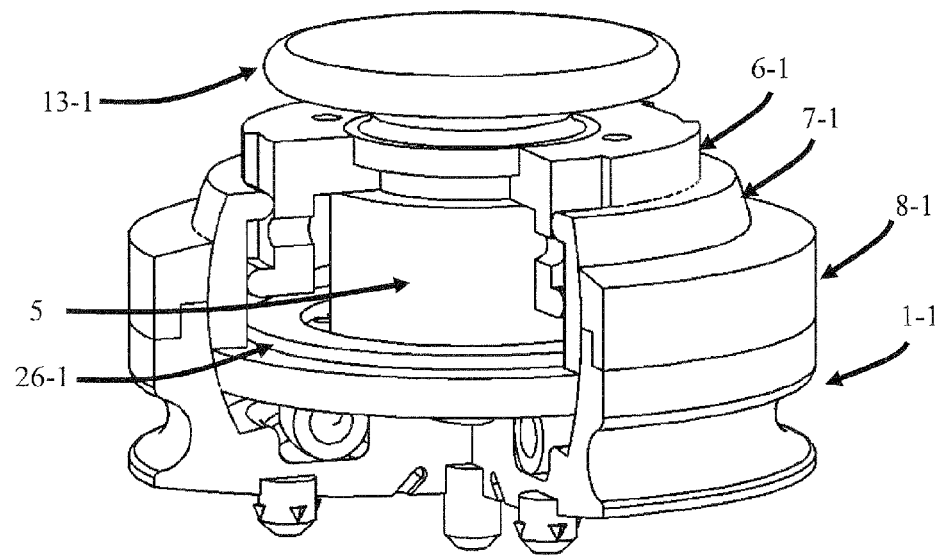

FIG. 25 depicts usage of a general spring/cushion core element 5, which can be any of the representative types in FIG. 26 and FIG. 27.

Figures 26A, 26B:
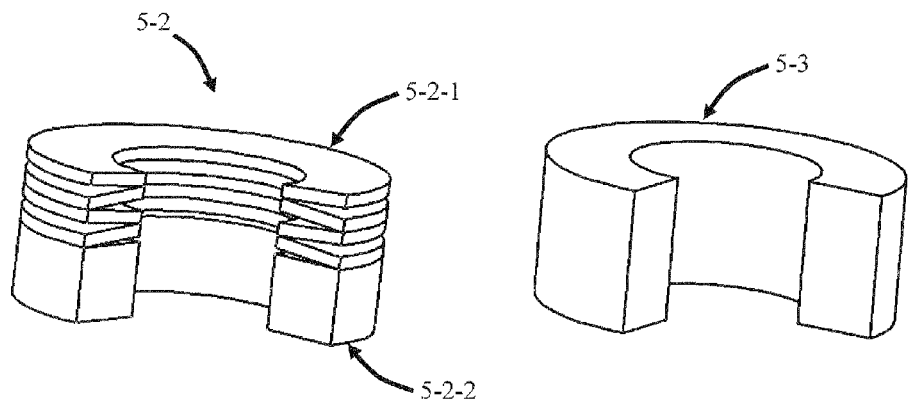
Figures 27A, 27B:
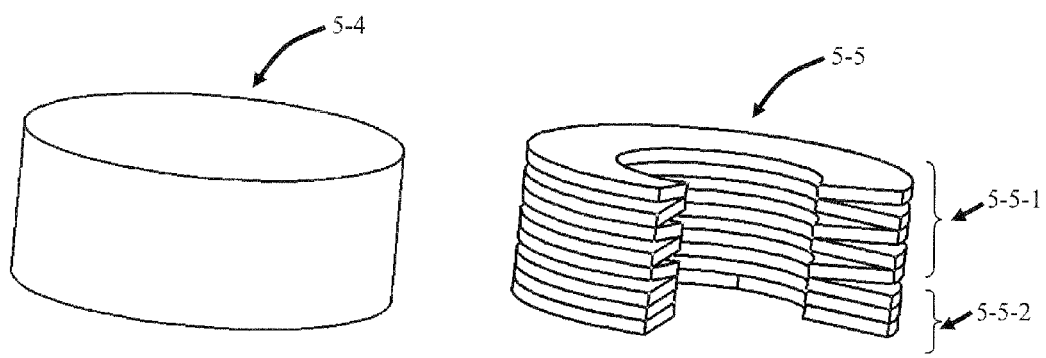

FIGS. 26A and B and FIGS. 27A and B depict a variety of spring/cushion core embodiments. FIG. 26A depicts an embodiment of a spring/cushion element 5-2 comprising a flexible, elastomer core 5-2-2 supporting a stack of Belleville springs. In another embodiment, the order of stacking is reversed. FIG. 26B presents an embodiment of a spring/cushion element 5-3 comprising an elastomer core with cylindrical hole for mandrel elements to pass. FIG. 27A illustrates an embodiment of a solid elastomer core 5-4 in an embodiment that does not use mandrel elements, and FIG. 27B illustrates an embodiment of a stack of Belleville disc springs 5-5 arranged in a series 5-5-1 and parallel 5-5-2 arrangement. Resistance against extension motions can be realized by fixedly attaching the superior surface of elastomer core 5-3 or 5-4 to the piston cavity ceiling and the inferior surface to surface 3-1-1 of the ball platform 3-1.

DETAILED DISCLOSURE

The subject invention provides devices that are capable of providing motion with up to six independent degrees-of-freedom. Embodiments of the device can further simultaneously provide reaction to compressive, tension and torsion loads. More specifically, the subject invention provides devices capable of approximating the natural motion that occurs between two vertebrae in a patient's spine.

The devices of the subject invention are useful in the medical fields encompassing spinal surgery. In particular, the subject invention provides devices and methods for correcting, replacing, or approximating movement between two vertebrae within a spine, i.e., a Functional Spinal Unit (FSU). More specifically, the embodiments disclosed herein can be useful for the treatment and/or removal of spinal disk herniation. While the subject application describes, and many of the terms herein relate to, a use for implantation within a spine, particularly for the treatment of spinal disc herniation, other uses and modifications therefor that will be apparent to a person with skill in the art and having benefit of the subject disclosure are contemplated to be within the scope of the present invention.

In order to provide a clear and consistent understanding of the specification and claims, including the scope to be given such terms, the following definitions are provided:

The term "Functional Spinal Unit" or "FSU", as used herein, refers to a physiological unit of a spine that includes two adjacent vertebrae, an intervertebral disc and all naturally occurring adjoining ligaments between the vertebrae. An FSU typically does not include surrounding tissues, such as muscles, vascular tissue, such as veins or arteries, or nerve tissue.

The term "patient" as used herein, describes an animal, including mammals, to which the systems and methods of the present invention are applied. Species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

As used in the subject application, "kinematic chain", "kinematic linkage", and "kinematic connection" refer to mechanical linkages, which inseparably, operably, and serially connect component elements of the subject invention to achieve the motion requirements described herein. It is known to those with skill in the art that a serial "mechanical linkage" is a series of joints connected with physical links to form a closed and/or open chain. Thus, as will be described herein, the components of the subject invention are inseparably linked, such that the components can move relative to each other, but no joint in the sequence can become separated during the motion. That is, when assembled and implanted in an FSU, the multiple internal joints formed by the components of the device of the subject invention remain interconnected or physically, but operably, connected at all times to each other during the relative motion with each other and the vertebrae of the FSU. In one embodiment, the resultant kinematic chain links a superior plate to an inferior plate through a series of such connected joints. From superior to inferior plates, for a particular embodiment, these joints are: a planar pair joint, an axial prismatic joint orthogonal to the planar joint, and a spherical pair joint. These joints can employ lower order pairs, that is sliding surfaces, or higher order pairs, which is the incorporation of ball bearings, roller bearings, sliding bearings, line bearings, fixed bearings, and so forth. In this disclosure, higher order pairs are not discussed as this is addressed elsewhere by Doty U.S. Pat. Nos. 7,361,192; 7,799,080; 7,927,375; U.S. Published Patent Application 2010/0324688 and U.S. patent application Ser. No. 13/157,539 (Doty) filed Jun. 10, 2011, which are hereby incorporated by reference, in their entirely, including any figures, tables, or drawings, and those techniques, as instructed therein, can be utilized with the embodiments of the subject invention by anyone skilled in the art.

In addition, the horizontal plane of the invention embodiments, and not the animal or human body FSU in which the device is implanted, is defined as a plane passing through the center of curvature 22 of ball 7-1, orthogonal to central axis 20 of the device, which also passes through 22 (see FIG. 7B, FIG. 8). A unit length vector along the intersection of a body frontal plane, which is perpendicular to the plane of the paper and passing through 20, with the invention's horizontal plane, can define a sagittal axis of the device, after a direction is selected, for example out of the page of FIG. 7B. A unit length vector along the intersection of a body sagittal plane (plane of the paper) passing through 20 with the invention's horizontal plane can define a lateral axis of the device, after a direction is selected, for example, from right-to-left in FIG. 7B. The central axis 20, perpendicular to the horizontal plane, the sagittal axis, perpendicular to the sagittal plane, and lateral axis, perpendicular to the frontal plane, define an orthogonal frame of reference with origin 22 fixed in the inferior plate 1-1. Arbitrary trajectories of superior plate 14-1 with respect to inferior plate 1-1 and within the FSU workspace, can be described in this reference frame and achieved by appropriate time varying motions of the joint mechanisms of the devices of the subject invention. Note, piston axis 21 rotates with piston 25, whereas central axis 20 is one of the "fixed" axes in the above defined reference frame, that is, the inferior plate's body-attached frame.

Advantageously, when the superior and inferior plates of the devices of the subject invention are fixedly attached to superior and inferior vertebra of an FSU, respectively, the kinematic chain provides an unbroken structure from the superior to inferior vertebra that operates for all nominal workspace motions naturally permitted by the disc the device of the subject invention replaces.

The present invention is more particularly described in the following embodiments and examples that are intended to be illustrative only since numerous modifications and variations thereof will be apparent to those skilled in the art. As used in the specification and in the claims, the singular for "a," "an" and "the" include plural referents unless the context clearly dictates otherwise.

Finally, reference is made throughout the application to the "cranial end" and "caudal end." As used herein, the cranial end 100 of any element described herein is that end that would typically be nearer to the head of a patient. Conversely, the caudal end 200 of any element described herein is that end that would typically be nearer to the tail end of a patient, for a human this would be the coccyx.

Various embodiments disclosed herein allow up to six independent degrees-of-freedom throughout the Functional Spinal Unit (FSU) workspace and simultaneously allow reaction to compressive, tension and torsion loads. The embodiments of the invention pertaining to approximating the potential motion between two vertebrae in an animal spine can maintain the integrity of the variable intervertebral spacing required during motion. For example, under compression, the intervertebral gap can narrow some and under tension it can widen some. During normal motion of the affected FSU, the system retains an unbroken, fully connected at all times, mechanical linkage between a superior and an inferior vertebra. Specifically, each surface in a kinematic pair can be chained or linked to the other without interfering with nominal joint motion of that pair. This feature promotes joint stability and assists in preventing the common problem of spondylolisthesis of the FSU during workspace motion. When appropriately scaled, the devices of the invention track FSU workspace movements, within prescribed joint limits, for up to three independent translational and three independent rotational motions of the superior vertebra with respect to the inferior vertebra of an FSU. In a patient, the subject invention provides, through appropriate mechanical programming of joint stops and scaling, a disc prosthesis for an FSU at any point along the spine. For example, in a human patient, the device, with appropriate joint stops and scaling can be utilized as a disc prosthesis from the cervical to the lumbar regions.

In one embodiment, the contour curve generated by a horizontal plane of the device intersecting surface 1-1-5 and/or surface of groove 14-1-6 can be a circle. In alternative embodiments, it can be polygonal or curvate or a combination of such curves. Ideally, with any of these embodiments, the resultant superior and inferior plates provide cavities congruent to inferior plate cavity 1-1-11 and planar socket cavity 14-1-2. A ball retainer, whose inner spherical surface can be the same as that of 8-1-3, can extend inner spherical surface 1-1-2 in a smooth continuous manner as before and its contour can be modified to mate with the modified inferior plate. No modifications to the planar retainer will usually be required for these variations, as long as all the cavities of the superior plate are congruent in those variations. These various geometries, as described, can affect the external shape of the boot, boot fasteners and clamps, ball retainer, and the superior and inferior plates, but the internal joint mechanisms can remain the same as in the embodiments depicted herein.

Contours of horizontal cross sections of superior plate cavity surface 14-1-3 and piston head surface of the lip 13-1-2 in a preferred embodiment are interdigitated circles, but they can also be interdigitated polygonal or curvate shapes, or a combination of such curves. In such cases the planar pair will have a range of motion that can be dictated by the offset between the horizontal cross section contours of surfaces 14-1-3 and 13-1-2. In other words, the interdigitated shape and depth of these surfaces can dictate the range of motion provided to the piston head 13-1.

The FSU angular and translational displacement along the various degrees of freedom, as instructed in the following description and examples, typically relate to cervical spine applications of the invention in a human patient. However, the invention is not restricted to the cervical spine and can be scaled and the internal joints can be appropriately joint limited for larger FSUs, such as, for example, L4-L5 in the lumbar region.

Figure 1:
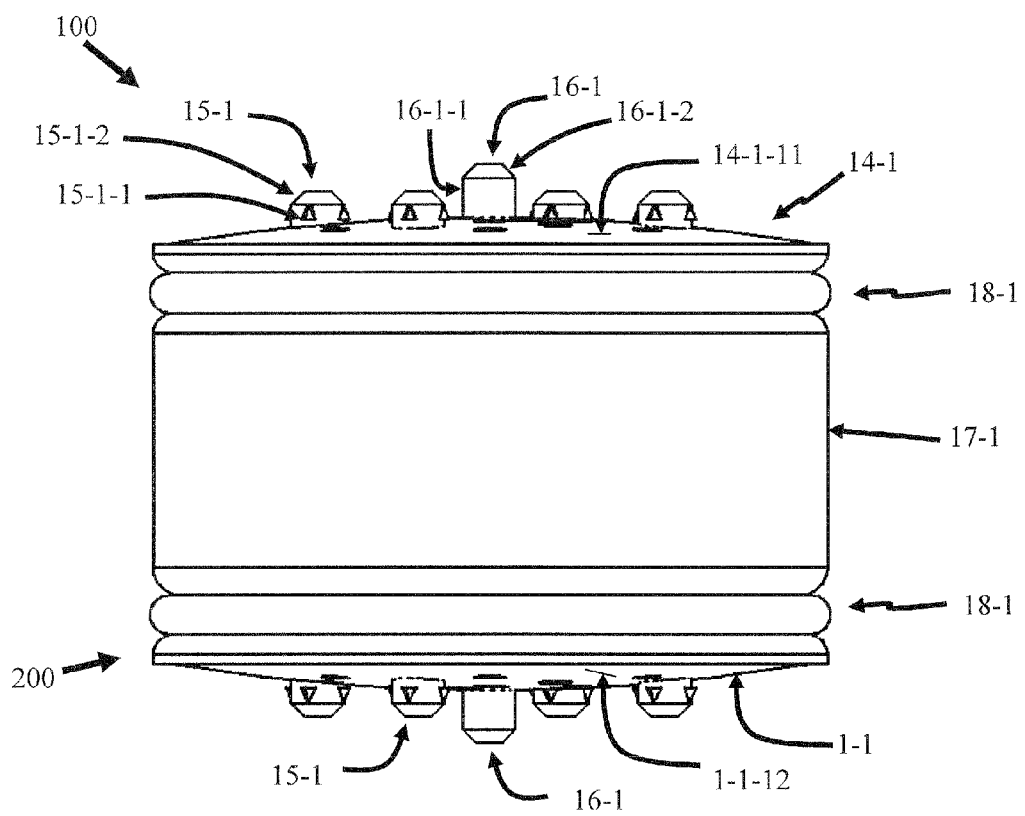
FIG. 1 depicts an assembled particular embodiment of a disc prosthesis of the subject invention in perspective elevated view. Visible elements of this embodiment include: superior plate 14-1; inferior plate 1-1; a fiber-reinforced, flexible, multi-layered resilient boot 17-1; clamping bands or rings 18-1: peripheral guide pins 15-1; and central guide pin 16-1.

The overall, external appearance of one embodiment of the invention in perspective elevation (FIG. 1) reveals the boot 17-1, boot clamping elements 18-1, inferior and superior plates 1-1 and 14-1 (FIG. 9 and FIG. 17) and the plate central guide pins 16-1 and a plurality of peripheral guide pins 15-1, four in the diagram. In one embodiment, the central guide pin is between approximately 0.25 mm and approximately 1 mm longer than the peripheral guide pins, which allows them to engage a pilot hole before any of the peripheral guide pins engage their pilot holes, ensuring appropriate centering of the prosthesis.

Guide pins assist in the accurate placement of the prosthesis within an FSU and provide immediate stability of a disc arthroplasty after insertion. For example, peripheral guide pins can define two orthogonal axes to establish a particular orientation of the device. The two orthogonal axis can be distinguished from one another during placement by the following. In a particular embodiment, eliminate one guide pin posteriorly on the lateral axis in the sagittal plane. Such a pin configuration immediately and visibly determines the insertion orientation of the device and can be easily determined with a casual glance, and, thus, can make insertion error extremely unlikely. During insertion the device can be turned about until the pilot holes for the peripheral guide pins, if any, match up. At that point, the device is centered and properly aligned and can be fully inserted. For cylindrically symmetrical embodiments of the device, centering the device alone with the central guide pin is sufficient for proper implantation. Use of a plurality of peripheral guide pins in a symmetric embodiment, however, can continue to serve as device insertion stabilizers.

Central guide pins 16-1 or 1-2 can be centered on inferior and superior surfaces 1-1-12 and 14-1-11 on the inferior and superior plates, respectively. Central guide pins can be screwed or press fit into pin cavities 1-1-8 and 14-1-8. The placement of the pilot holes for the superior and inferior plate central guide pins can be such that the central axes of those pins (and holes) coincide with each other and the central axis 20 (FIG. 8) of the FSU involved.

When the central axes of the superior and inferior plate central guide pins of an implanted device within an FSU coincide, i.e. with central axis 20, then that configuration of the embodiment, with spring/cushion elements 5 only partially compressed by cranial loads, defines a typical neutral position of the planar, prismatic and spherical joints within the embodiment (FIG. 8). All motion capabilities of each joint are referenced to this typical neutral position (refer to FIG. 7). For example, the fixed central axis 20 (FIG. 8) and ball polar axis 21 (FIG. 20), which is usually the same as the piston axis (FIG. 16), can coincide with the central guide pin axes and the disc's central axis 20 when an implanted device and its FSU are in the typical neutral position. This is a preferred configuration for implanting a particular embodiment of the subject invention within an FSU.

The number and distribution of the plurality of peripheral pins on the inferior and superior plates can vary. A particular embodiment can use four peripheral pins, two of whose centers can line up with the center of the central guide pin and can lie in the sagittal plane of the device. The centers of the other two can also line up with the center of the guide pin and can lie in the device's frontal plane. A three guide pin configuration, described previously, eliminates the posteriorly located guide pin whose center axis lies in the sagittal plane. In a further embodiment, the guide pins can have indents, cavities, or fissures 16-2-1 and 15-2-1, for bone ingrowth. In an alternative embodiment, the guide pins can have a smooth barrel 16-1-1 and barbs 15-1-1 (FIGS. 23A and B). In a still further embodiment, guide pins can be chamfered or otherwise tapered, such as shown, for example, in FIGS. 23A and B as 15-1-2, 16-1-2, 15-2-2, and 16-2-2.

Before implantation of the prosthesis, the inferior and superior vertebrae of an FSU can be prepared by abrading slightly concave and convex spherical depressions to conform to surfaces 1-1-12 and 14-1-11, respectively, and by drilling pilot holes for all the guide pins. Inferior and superior surfaces 1-1-12 and 14-1-11 can alternatively be covered with fixedly attached micro-screen titanium mesh or covered with a titanium micro-particle vapor deposit to promote bone fusion. Micro meshes typically used in reconstructive surgery can be approximately 0.1 mm thick and be bonded to the plates. In a further embodiment, the plates can be made of titanium or an alloy of titanium. Central guide pin holes should be drilled to allow easy, but not sloppy, insertion. When one or more peripheral pins have barbs, a smooth barrel 16-1-1 central guide pin 16-1, which can extend further than the peripheral guide pins, advantageously allows rotation of the device about central axis 20 during insertion, until chamfered ends 15-1-2 and 15-2-2 of peripheral guide pins engage their drilled holes. Peripheral guide pins 15-2 can have a slight taper or tighter hole tolerances to engage cancellous bone more securely, while versions 15-1 do not require either a taper or tight hole tolerances, as long as the barbs extend enough to engage cancellous bone to secure the device to the bone immediately. The barbs 15-1-1 can also have a pyramidal shape that appears to embed into the barrel of the guide pin. This shape advantageously provides the combination of a sharp edge and a larger engagement of bone to oppose greater extraction forces.

In addition to central guide pin 16-1, pin cavities 1-1-8 and peripheral guide pins 15-1, and pin cavities 1-1-7, the inferior plate 1-1 can also have a plurality of micro-holes 14-1-9 etched or drilled into the inferior surface 1-1-12 at various angles to provide for bone growth and increase the bond to an inferior vertebra of an FSU. Such holes can be used to fix the plates to the vertebra in lieu of or in addition to titanium micro mesh or titanium micro-particle vapor deposit. In like manner, the superior plate 14-1 can have central guide pin 16-1 pin cavity 14-1-8 and peripheral guide pins 15-1 pin cavities 14-1-7, which can be threaded or designed for press fit of the pins, as is the case for 1-1. The superior plate can also have bone fusion-holes 14-1-9 etched or drilled into the surface at various angles to provide for bone ingrowth and bonding to the superior vertebra of an FSU. In another embodiment, the central and peripheral guide pins can be milled/cast/stamped as part of the plates 1-1 and 14-1. In one embodiment, the bone fusion cavities are drilled into the surface of the superior and inferior plates at an angle that is less than 90° relative to those surfaces, such as shown, for example, in FIG. 9 and FIG. 17.

In one embodiment, the inferior and superior plates 1-1 and 14-1 of the subject invention have revolute body structures, that is, a body structure created by revolving a planar region about an axis. Non-revolute structures can also be employed to encapsulate the same or similar internal structures, features, and joints. While these embodiments are not elaborated on herein, the preparation of such variations would be clearly understood by one skilled in the art having benefit of the subject application, as well as reference to U.S. patent application Ser. No. 13/157,539 (Doty) filed Jun. 10, 2011.

In one embodiment, the interior mechanisms of the invention are protected by a tough, possibly multi-layered, fiber reinforced, flexible boot 17-1. In a further embodiment, the fiber weave has a diamond pattern to mimic the fiber structure of the annulus fibrosus of a natural disc. Such a boot can be tightly clamped to the inferior plate 1-1 and superior plate 14-1 by clamping elements 18-1. The boot can have multiple functions, such as, but not limited to, providing restoring torques and tension forces to oppose those generated by the muscles and internal spring elements of the device; sealing out fluids; sealing in fluids; protecting the mechanism from bio-fouling; and providing tension to oppose extension of an FSU. Other methods and devices can also be used for attaching the boot to the plates, such as, by way of non-limiting examples, grommets and rivets, multiple screws on boot edge clamps, or combinations thereof in possible conjunction with the previously described clamping elements.

The exploded view of a generalized embodiment of the device in FIG. 2 depicts the elements in the order in which they can be stack assembled (FIG. 21), meaning that all elements can be stacked on each other in the manner shown to assemble this embodiment of the device.

In this embodiment, a stack assembly can be achieved, by way of example, as follows (refer to FIG. 21): 1) insert rotation cushion 2-1 and ball platform 3-1, including inferior mandrel 4-1 with spring/cushion elements 5 (spring cushion element 5-1 is shown, for example) stacked thereon, into inferior plate major cavity 1-1-11 (FIG. 13); 2) drop ball 7-1 over cylinder 6-1 and slip ball retainer 8-1 over both, letting it drop to equator 24 (FIG. 20); 3) insert piston head 13-1 and superior mandrel 12-1 as an integrated unit, with flexible planar cushions 10-1 and 11-2 slipped around neck 3-1-8, into cavity 14-1-2 of superior plate 14-1 with piston planar surface 13-1-1 contacting superior plate surface 14-1-1; 4) fixedly attach planar retainer 9-1 into recess 14-1-4 and 14-1-10 provided for it on superior plate 14-1, thereby retaining piston head 13-1 in that cavity while allowing planar motion between surfaces 13-1-1 and 14-1-1; 5) insert superior mandrel 12-1-1 and piston shoulder and superior mandrel base, 13-1-4 and 13-1-5, respectively, into orifice 6-1-9 of cylinder 6-1 and fixedly attach or press fit into recess 6-1-1 of cylinder 6-1 to realize the piston configuration 25 plus planar cushions; 6) fixedly attach or press fit ball retainer 8-1 to inferior plate 1-1 to complete the assembly; 7) finally, slip boot 17-1 over assembled device and attach clamping elements 18-1, the later is not non-stacking operation. The upper stack assembly, described in steps 1-2 and lower stack assembly, described in steps 3-6, can then be stacked together to complete the device assembly, except for the boot, which is assembled in step 7. Stack assembly can provide considerable economic advantages in manufacture.

From the assembly example provided above, it should be clear how all the joints preserve their operational integrity throughout workspace motion and limit the ranges of these motions according to the mechanical joint limits provided.

In one embodiment, rotation cushion 2-1 (FIG. 12) is a tubular shaped piece that lies below ball platform 3-1 (FIG. 3, FIG. 7, FIG. 8, and FIG. 13) and can interfere with rotation of 3-1 within the cavity of 1-1, thus providing resistance to rotations and cushioning torsion shocks to the unit for any rotations about an axis perpendicular to the rotating axis 21 and passing through center of curvature 22. The rotation cushion can comprise a polyurethane or polyetheretherketone or other flexible thermoplastic elastomer. Rotation cushion 2-1 can also be filled with compressible or non-compressible biocompatible gas/fluids/gels or comprise a hydrophilic artificial nucleus element. Alternatively, it can be a solid, compressible elastomer. In one embodiment, a choice of one of spring/cushion elements 5-1, 5-2, 5-3, or 5-5, shown, for example, in FIG. 24, FIGS. 26A and B, and FIGS. 27A and B, can rest on ball platform 3-1, and can be centered by segmented-wall inferior mandrels 4-1. In a further embodiment, piston 25 slides down over and encloses spring/cushion elements 5-1, 5-2, 5-3, or 5-5 and centers those elements from the top with segmented-wall superior mandrel 12-1. Together, inferior and superior mandrels 4-1 and 12-1 can form a complete columnar support for those same spring/cushion elements as the piston 25 moves up and down along its own central axis 21. The plurality of segmented walls 4-1-1 and 12-1-1 (FIG. 10 and FIG. 14) of the two mandrel elements 4-1 and 12-1 can alternate, with gaps 4-1-2 that accommodate the walls 12-1-1 of the superior mandrel 12-1, and cavity and wall gaps 12-1-3 that accommodate inferior mandrel wall segments 4-1-1 and solid center 4-1-3 of the inferior mandrel, so the two mandrel elements can slide by each other without interference along the piston axis 21. In a specific embodiment, when the inferior and superior mandrel elements each have an effective height h, the columnar mandrel comprising the two can collapse down to height h at maximum compression of the spring/cushion element and extend to almost 2 h minus some overlap provided by chamfered ends 12-1-2. At maximum extension of the cylindrical prismatic joint, inferior and superior mandrel wall segments can overlap at a minimum, but they can still provide continuous columnar central support for spring/cushion elements. In a particular embodiment, each mandrel element has three wall segments for a total of six wall segments in the column. In a more particular embodiment, each wall segment is a sixth of a right circular cylinder, subtending 60 degrees of arc. Walls 12-1-1 of segmented wall superior mandrel 12-1 can have chamfered, or curvate tapered, ends to help center spring/cushion elements 5-1, 5-2, 5-3, or 5-5 as the piston 25 strokes up and down parallel to its own central axis 21.

In an alternative embodiment, each mandrel element has two wall segments for a total of four wall segments in the column, each wall segment occupying alternative quadrants of a right circular cylinder. The plurality of wall segments can vary in number and subtended angle, but the net angle subtended at the column surface of all the wall segments generally does not exceed 360 degrees. Ideally, regardless of the number of wall segments or net angle that they encompass, the segments do not interfere with each other during the required relative sliding motion of the inferior and superior mandrel elements along cylinder axis 21.

In a further embodiment, ball retainer 8-1 slides down over ball 7-1 to the equator 24 and comes to rest during the assembly process (FIG. 20). The lower inside edge 8-1-8 of ball retainer 8-1 defines a great circle of a sphere with the same radius 23 and center of curvature 22 as the ball spherical surface 7-1-1. Thus, with this embodiment, when the outer rim 1-1-13, which is part of the lower recess 1-1-4 of inferior plate 1-1 is fixedly attached or press fit into ball retainer recess 8-1-6 defined by surfaces 8-1-4 and 8-1-5, ball 7-1 becomes locked into a socket comprising a spherical cavity formed by the retainer inner spherical surface 8-1-3 and inferior plate spherical surface 1-1-2 with the same radius 23 and center of curvature 22 as the ball spherical surface 7-1-1.

In this embodiment, the ball retainer 8-1 and the rotation limits imposed on rotations about the sagittal and lateral axes by ledges 1-1-3 and 1-1-10, confines the ball 7-1 within the socket of inferior plate 1-1. Specifically, the ball element and the combined socket element spherical surfaces 8-1-3 and 1-1-2 both included the equator (a great circle of the defining sphere) of the ball-and-socket joint. Since the open end of the socket is smaller than a great circle, the ball 7-1 cannot be withdrawn from the socket under non-destructive forces. Additionally, ledges 1-1-3 and 1-1-10 prevent the spherical shell constituting the ball from being rotated out of the socket and extracted. Ball 7-1, in turn, can confine rotation cushion 2-1 and ball platform 3-1 within the cavity of the inferior plate 1-1.

In a further embodiment, ball 7-1 and ball-platform 3-1 limit the down-stroke of the piston 25 (FIG. 16) along central axis 21. Bearing interlocks 7-1-4 and 6-1-7 can also limit the upstroke of piston 25 along central axis 21. In a particular embodiment, a washer cushion 26-1 (FIG. 24), whose annulus can be the thickness of cylinder wall 6-1-3, of selectable height, and resting on surface 3-1-1 of ball platform 3-1, cushions the impact of cylinder 6-1 with ball platform 3-1 during an extreme compression stroke of piston 25. The height of washer cushion 26-1 reduces the range of the piston down stroke. Spring/cushion elements 5-1, 5-2, 5-3, or 5-5 and mandrels 4-1 and 12-1 can also be confined within the cavity created between the ball platform 3-1 and the piston 25. Piston 25 can be confined within superior plate 14-1 by the planar retainer 9-1. Consequently, a particular embodiment of the invention maintains a continuous, inseparable, but functionally operational, kinematic chain of lower-level pair joints between inferior and superior plates that realizes six independent degrees of freedom, three translational and three rotational. The following discussion explains how embodiments of the invention realize these degrees-of-freedom.

In a particular embodiment, planar pair (13-1-1, 14-1-1) realizes two orthogonal degrees of translational freedom since the piston head can move freely in polar coordinates (r, θ), within the constraints defined by the relative sizes of piston head 13-1 and superior plate cavity 14-1-2. With the origin of the polar coordinate frame at the intersection of piston planar surface 13-1-1 with axis 21 and the device in a neutral position, superior plate 14-1, in a particular embodiment, can move, relative to that origin, approximately 1 mm in the radial direction r at any angular direction θ defined with respect to a specified reference. Different geometric shapes of piston head 13-1 and compatible geometries of superior plate cavity 14-1-2 can be devised by one skilled in the art to create a plurality of motion capabilities. For example, as instructed in U.S. patent application Ser. No. 13/157,539, which has previously been incorporated by reference, a rounded-corners square shape of both piston head and cavity can lead to independent rectangular motion of approximately ±1 mm in the x-direction and approximately ±1 mm in the y-direction. As another non-limiting example, piston head 13-1 has a circular horizontal cross-section while cavity 14-1-2 has an elliptical horizontal cross-section, with the major axis in the sagittal plane and the minor axis in the lateral plane. Such a configuration restricts lateral translations and has maximum range for translations during flexion and extension where it is most needed. Other geometric alternatives can easily be deduced from this instruction by one skilled in the art.

A plurality of tubular, or otherwise shaped, planar cushions compatible with cavity/bearing-raceway 13-1-3 can resist motion in the planar joint and provide shock absorbing characteristics. In a particular embodiment, toroidal cushions 10-1 and 11-1 can nestle within raceway 13-1-3 of piston head 13-1 (FIG. 8) and resist translational motion of the superior plate 14-1 in the plane of piston planar surface 13-1-1 and superior plate planar surface 14-1-1. This resistance results from curvate surface 9-1-4 of planar retainer 9-1 compressing the tubes as superior plate 14-1 moves about the plane. Toroidal tubes 10-1 and 11-1 can also provide shock absorption for sudden motions in the plane by the superior plate 14-1. The difference in radii of curvature between the two toroidal planar cushions 10-1 and 11-1 and the thickness and elasticity of the tubes and contents, are able to dictate the amount of compression at maximum travel. Planar cushion tubes can be manufactured from various thermoplastics, such as, for example, polyurethane, and can further be filled with fluid/gas/gel or combinations to generate desirable compression characteristics. Alternatively, they can be highly compressible solid elastomers. Planar cushions reduce the amount of travel of the superior plate with respect to the piston head and, thus, provide a further means for controlling planar joint stops.

The prismatic joint realized by the motion of the piston 25 along its own central axis, i.e., the piston axis 21, can be perpendicular to the plane of the planar joint for all motions and adds a third independent degree of translational freedom. Maximum extension of this joint can be controlled by a plurality of bearing interlocks 6-1-7 on cylinder 6-1 and a plurality of bearing interlocks 7-1-4 on ball 7-1. A fiber reinforced, multi-layered, thermoplastic boot 17-1 can also help resist extension.

In one embodiment, a plurality of first bearing interlocks 6-1-7 blocks the caudal ends of a plurality of bearing raceways 6-1-6 cut into wall 6-1-3 of cylinder 6-1, while a plurality of second interlock bearings 7-1-4 block the caudal ends of a plurality of bearing raceways 7-1-5 cut into interior wall surface 7-1-3 of 7-1. The plurality of bearing raceways 6-1-6 and 7-1-5 can match against each other to provide a raceway for interlocking bearings 6-1-7 along 7-1-5 and a raceway for interlocking bearings 7-1-4 along 6-1-6. At maximum upward stroke of piston 25 (shown in cross-section in FIG. 7C), bearings 6-1-7 and 7-1-4 can interfere, halting further extension. Although the diagrams indicate bearings 7-1-4 and 6-1-7 as sliders, in alternative embodiments, they can be roller bearings held within bearing retainers, which are fixedly attached to 7-1 and 6-1, respectively.

Extension motions past neutral, not just at extreme extension, can also be resisted in embodiments with elastomers spring/cushion core elements, such as 5-3 or 5-4 (FIG. 26 and FIG. 27), when their ends are fixedly attached to the piston cavity ceiling and ball platform surface 3-1-1.

Ball retainer 8-1 does not allow ball 7-1 to be pulled out of the socket under nominal extension loads, hence, in turn, the interlocking bearings 7-1-4 and 6-1-7 will prevent further extension of piston 25. The interlocking bearings acting in this manner serve as extension joint stops. Positioning bearings 6-1-7 at various locations on raceways 6-1-6 can control the maximum permissible extension of the prismatic joint along the cylinder's central axis 21. Ball platform 3-1 and elastomer washer elements 26-1, limit the downward stroke of the piston (shown in cross-section in FIG. 7A) and limit the maximum permissible compression of the prismatic joint or the device itself. For an example of the latter, an axial shock in the neutral position might completely compress the device to its minimum height.

Spring/cushion elements 5 can resist downward strokes of the central hydraulic cylinder and fit within cylinder cavity 6-1-4 at maximum compression. Segmented-wall, inferior and superior mandrels 4-1 and 12-1, can provide columnar support and help center the spring/cushion elements 5-1, 5-2, 5-3, or 5-5 during operation. In a particular embodiment, no superior or inferior mandrels are used with elastomer cores 5-3 (FIG. 26B) or 5-4 (FIG. 27A). Inner bottom edge 6-1-11 (FIG. 15) of cylinder central cavity 6-1-4 can be chamfered to assist the mandrel elements, where employed, in centering spring/cushion elements 5 during a downward stroke of the piston.

As a cervical FSU moves into flexion, the intervertebral space compresses due to the forces and moments-of-force involved. Spring/cushion elements 5 (FIG. 24, FIG. 25, and FIG. 26) can resist this motion to add resiliency and joint shock absorption. In one embodiment, spring elements are a set of Belleville springs 5-1-1 arranged in a series 5-1 (FIG. 22), or series-parallel configurations, for example 5-5 (FIG. 27B), with possibly different spring constants. Elastomer cores such as 5-3 (FIG. 26B) and 5-4 (FIG. 27A) can also be used separately or in combination with spring elements 5-2 (FIG. 26A). Elaboration of Belleville spring usage and modifications are given in US Published Patent Application No. 2010/0324688, which has been previously incorporated by reference. Belleville springs can be manufactured from various biocompatible materials. By way of non-limiting example, various bio-inert stainless steel and titanium alloys can be used for Belleville spring elements.

Ball 7-1 and ball platform 3-1, together with the inferior plate 1-1 and ball retainer 8-1, can realize a three independent rotational degrees-of-freedom ball-and-socket joint. Spherical surfaces 7-1-1, 3-1-4, 1-1-2, and 8-1-3 can have the same center and radius of curvature. In a particular embodiment, spherical segment 3-1-1, centrally and fixedly attached under ball platform 3-1, or machined or molded as part of the platform, rests in spherical cavity 1-1-1 (FIG. 13, and FIG. 7). Spherical surfaces of 3-1-1 and of cavity 1-1-1 can have the same center of curvature. The radius of curvature of 3-1-1 and 1-1-1 can be the same, but that radius can be considerably smaller than the radius of curvature of ball 7-1. Elements 3-1-1 and 1-1-1 form a secondary ball and socket joint that work in concert with the larger one involving 7-1, in which case the common center of curvature 22 of spherical surfaces 3-1-1 and 1-1-1 coincides with that of spherical surfaces 8-1-3, 7-1-1, 3-1-4, and 1-1-2. The ball 7-1 can be fixedly attached to the ball platform 3-1, but, whether it is or not, ball platform 3-1 and rotation cushion 2-1 below it will be confined to inferior cavity 1-1-11 by the ball 7-1, which in turn, is retained within the socket of 1-1 by ball retainer 8-1. Hence, all elements caudally located with respect to the ball remain within socket of inferior plate 1-1 during all joint operations.

Ledges 1-1-3 and 1-1-10 (FIG. 9) have the same slope with respect to the horizontal plane of the embodiments of the invention (not the body) and that slope can be set equal to the maximum angle of rotation permitted by the embodiment about any axis perpendicular to 21 and passing through the center of curvature 22. Such an axis, which rotates as axis 21 rotates, yields two independent rotation freedoms of motion. As ball platform 3-1 rotates within sockets of 1-1, its underside can come into contact with those ledges. At contact, ledges 1-1-3 and 1-1-10 interfere with any further tilting of the ball-platform 3-1 in a particular plane of rotation. Thus, those ledges determine the allowable, maximum, absolute angle deviation, or tilt $\theta$ (FIG. 7), of the piston axis 21 from the device central axis 20. Superior plate 14-1, however, can be free to rotate about piston axis 21 regardless of its tilt $\theta$, thus, providing a third independent rotation. The three independent translational motions derived from the planar pair joint and the piston prismatic joint then accommodate any additional displacements of the superior plate 14-1 with respect to the inferior plate 1-1 not generated by the rotation motions about center 22.

As ball platform 3-1 rotates or tilts, resilient toroidal cushion element 2-1 resists compression by the platform, and, consequently, resists torsions acting on superior plate 14-1 about an axis perpendicular to 21 and passing through the center of curvature 22. Rotations about axis 21 usually have no effect on tilting the ball platform or compressing the rotation cushion. Collapse of a portion of 2-1 at full compression or full extension can be observed in cross sections shown in FIG. 7A and FIG. 7C. In one embodiment, a polyurethane toroidal tubular structure filled with compressible or non-compressible fluid/gas/gel transfers the pressure to the cavity volume opposite the rotation and absorbs energy during normal operation and in the case of a sudden, or possibly traumatic, rotation. The durometer and flexibility of biocompatible polyurethane or other thermoplastic material dictates the degree of the cushioning and torsion resisting effects of rotation cushion 2-1 and whether the ball platform 3-1 actually tilts to the ledge hard stops 1-1-3 and 1-1-10. In a particular embodiment, the rotation cushion 2-1 can be a compressible solid elastomer. The rotation cushion, in another embodiment, consists of an artificial disc nucleus material of suitable geometric shape that encircles platform 1-1-13, a structure that supports ball 3-1-1 of the ball platform 3-1 when placed into socket 1-1-1 of the inferior plate 1-1. Two alternative geometries are toroidal or a non-closed linear segment that wraps around the full circumference of platform 1-1-13 with a small gap. Such artificial disc material can be hydrophilic and operate similarly to a natural disc when used according to the subject invention, except that axial compression forces are taken care of primarily by the spring/cushion elements 5.

FIG. 3 is a partial quadrant-cutaway of a cylindrical embodiment of the invention in the neutral position that highlights specific characteristics of the internal mechanism just described. The piston head 13-1, superior mandrel 12-1, inferior mandrel 4-1, and the ball platform 3-1 are not cutaway in this view. Half of boot 17-1 and its retaining elements 18-1 are cutaway in this view. Some of the disc springs are shown cutaway and others at the top are shown whole. Radial distance 19 (FIG. 3 and FIG. 8) from any point on lip 13-1-2 to a corresponding point on cavity recess 14-1-3 of a particular embodiment that realizes circular boundaries for both piston head 13-1 and superior plate cavity 14-1-2, varies from approximately 0.8 mm up to approximately 1.5 mm for a cervical disc replacement, depending upon the number of planar cushion elements 10-1 and 11-1 employed and the inner diameter of bearing raceway, or "neck", 3-1-8 on the piston head 13-1. The use of a single planar cushion element 11-1 can be a choice for a particular embodiment and is depicted here, but (FIG. 8) reveals a sagittal plane cross section of an embodiment in neutral that employs two planar cushions.

In the neutral position, for a particular embodiment (FIG. 8), interference bearing 6-1-7 locates approximately midway on bearing raceway 7-1-5. At full compression, bearing 6-1-7 moves to the extreme caudal end of raceway 7-1-5 and at full extension, to the extreme cranial end where it contacts and interferes with bearing 7-1-4 on ball 7-1 (refer to FIG. 7 to view these positions in cross section).

Typically, spring/cushion elements 5 are partially compressed in neutral, representing cranial and muscular loading on the prosthesis. Cushion elements 2-1, 10-1, and 11-2 will typically be in a relaxed state when the device is in neutral. Boot 17-1, when used, can be under tension in neutral. Boot 17-1 can be more flexible in anterior regions and gradually decrease in flexibility towards the posterior regions. It can also be reinforced with a diamond weave of flexible fibers arranged to maximally assist in torsion control for axial rotations. Various flexible thermoplastics, such as, for example, some polyurethanes, can be configured in this manner.

In one embodiment, when an FSU, with the invention implanted, executes an extension motion, superior plate 14-1 simultaneously rotates $\theta_2$ and slides $d_2$ toward the posterior of the FSU and piston 25 travels cranially along its own axis 21 (FIG. 7C). Spring/cushion elements 5 can gradually decompress, planar cushions 10-1 and 11-1 gradually collapse on the anterior side and expand on the posterior side, rotation cushion 2-1 gradually collapses on the posterior side and expands on the anterior side, and boot 17-1 stretches more on the anterior side than the posterior side. With this embodiment, the three cushion elements and boot resist extension motion from neutral, producing a restoring force to reconfigure the prosthesis to its neutral configuration as soon as cranial and muscular loads permit. Spring/cushion elements can also maintain the appropriate intervertebral gap in neutral under normal cranial and muscular loading, but allow anterior expansion of that gap during extension.

When an FSU, with a device of the invention implanted, executes flexion motion, simultaneously, superior plate 14-1 rotates $\theta_1$ and slides $d_1$ towards the anterior of the FSU and piston 25 slides caudally along its own axis 21 (FIG. 7A). Spring/cushion elements 5 gradually compress, planar cushions 10-1 and 11-1 gradually collapse on the posterior side and expand on the anterior side, rotation cushion 2-1 gradually collapses on the anterior side and expands on the posterior side, and boot 17-1 can stretch some on the posterior side and slacken on the anterior side. In this embodiment, the three cushion elements and boot resist flexion motion from neutral, producing a restoring force to help reconfigure the prosthesis to its neutral configuration as soon as cranial and muscular loads permit. Spring elements can generate faster restoring forces than cushion elements to realize the required intervertebral spacing as the prosthesis moves out of flexion into neutral. The devices of the subject invention allow anterior compression of the intervertebral gap during flexion.

Rotations involved in the extension and flexion motions with regard to the embodiment described in the preceding two paragraphs are about the sagittal axis, which passes through the center of curvature 22 and is perpendicular to, and out of, the plane of the diagram of FIG. 7, where in each case, the cross section plane is the central sagittal plane passing through axis 20. If each of these cross section planes in the descriptions of FIG. 7 is considered a frontal plane passing through axis 20, then those same diagrams depict left-lateral and right-lateral bending motions about the lateral axis, which passes through the center of curvature 22 and is perpendicular to, and out of the plane of the diagram. Rotations about the piston axis 21 are also permitted by the device. The flexion-extension and left-right-lateral rotation angles can vary by approximately ±10 degrees for a particular embodiment. The resultant relative position of the joint surfaces can be similar to those seen in the sagittal plane sections of FIG. 7. The following discussion generalizes this description of device motion capability.

General motion capabilities of a particular embodiment of the invention can be understood by considering FIG. 7 and the cylindrical symmetry of the device for the particular embodiment shown. Since the motion capability of the planar, prismatic, and rotational joints can possess, by construction, cylindrical symmetry about the central axis 20 in neutral configuration (FIG. 8), the motion capabilities exhibited by the cross sections of FIG. 7 can represent any plane passing through axis 20, not just the sagittal and frontal planes passing through axis 20, as described above. This symmetry of motion is not maintained when asymmetric joint stop elements are introduced into embodiments of the invention. For the symmetric case, accurate placement of the central guide pin within an FSU can assure a symmetric workspace for that FSU by a device of the invention. Placement of the peripheral guide pins can be guided by their pilot holes and a partially inserted central guide pin. Central and peripheral guide pins help secure the device within the disc space of the FSU. Workspace symmetry can make surgical implantation easier and more flexible. Where such symmetry is not clinically desirable, appropriate rotation and translational joint stops can be incorporated within the embodiment. In such cases, orientation of the peripheral guide pins about the center guide pin can matter and must be accommodated appropriately when implanting such a device within an FSU. For example, the posterior peripheral guide pin on superior plate 14-1 can be eliminated, thereby, uniquely identifying the proper orientation (right, left, anterior, posterior, superior, and inferior) of the device during insertion.

In one embodiment, in the neutral position, a line joining the tip centers of the central guide pins on the superior and inferior plates, defined as congruent with the central axis 20, can be approximately coincident to the central axis vector of the FSU for maximum workspace utility. However, depending upon the structural requirements of the patient, it may be necessary for the guide pins to be offset from the central axis. Surgically, one typically drills pilot holes, centered on the disc footprint of the superior and inferior vertebrae inferior and superior surfaces, respectively, which have been prepared to receive convex and concave surfaces of 14-1-11 and 1-1-12, in line with the central axis of the FSU, or aligned as required, for a particular patient.

Inclination of the devices of the invention with respect to the body coordinates will usually depend upon the natural inclination of the FSU to the body planes. Specifically, the devices can be inserted into an FSU, with the disc partially or fully removed. A convex surface that is approximately centered on the disc footprint of a superior vertebra of an FSU, can be ground to conform with convex surface 14-1-11. Maximum depth for this ground surface can be as small as approximately 0.5 mm. Center and peripheral guide pin pilot holes can be drilled into the prepared cancellous bone surface. At insertion, guide pins on convex surface 14-1-11 can be pressed into their respective pilot holes and 14-1-11 can fit snugly and securely against the convex surface.

A concave surface that is approximately centered on the disc footprint of an inferior vertebra of an FSU, can be ground to conform with convex surface 1-142. Maximum depth for this ground surface can be as small as approximately 0.5 mm. Center and peripheral guide pin pilot holes can be drilled into the prepared cancellous bone surface. At insertion, guide pins on convex surface 1-1-12 can be pressed into their respective pilot holes and 1-1-12 can fit snugly and securely against the concave surface.

The central guide pins 16-1 (16-2) can be longer than the peripheral guide pins 15-1 (15-2). In one embodiment, the central guide pin is inserted into the pilot holes approximately half a millimeter or more before the peripheral guide pins engage the cancellous bone. This method stabilizes the devices of the invention in the proper position and orientation within the patient's FSU as the guide pins press into the cancellous bone of the vertebrae. Proper placement of the devices of the invention between the vertebrae of an FSU maximizes the effective work space of the implanted prosthesis. With the superior and inferior plates mounted as instructed, the devices of the subject invention accommodate to the FSU workspace motion requirements and settle into a nominal working configuration compatible with the FSU workspace.

A person with skill in the art would be able to determine the appropriate number and placement of guide pins and/or similar structures with similar intended purpose.

Advantageously, the devices of the subject application can provide 1) effective static load bearing through central axis spring/cushion elements, for example, 5-1, 5-2, 5-3, 5-4, or 5-5 (FIG. 22, FIG. 26, and FIG. 27); 2) hydraulic damping and shock absorption by means of hydraulic pumping action by piston 25 of fluids/gases through hydraulic portals 3-1-6 and 6-1-8; 3) cushioning planar joint motions with toroidal cushion elements 10-1 and 11-1; 4) automatic hydraulic lubrication of all joints; 5) intervertebral stability and inseparability through mechanical linkage between a superior and an inferior plate that prevents motion outside the nominal, natural range; 6) mechanically programmable vertebral spacing under nominal compression load-bearing by appropriate selection of spring constants, height, number, and series/parallel configurations in a central spring element or stack and/or selection of an elastomer core; 7) 6-DOF motion tracking with variable disc height throughout the prosthesis workspace, as dictated by nominal disc operation, 8) a rotation cushion 2-1 for offering resistance to rotations about any axis perpendicular to axis 21, which can be rotating, and passing through center of curvature 22; and 9) a mechanically programmable prosthesis workspace through judicious sizing of linear, planar, and rotational joint stops and cushion elements.

A tough, but compressible cushioning device, such as, for example, hydrophilic, elastomer cushioning devices, medical polyurethane, polyetheretherketone or other biocompatible thermoplastic of appropriate durometer, or devices that function similarly thereto, can replace significant portions, or all, of the disc spring elements in a particular embodiment. The cushioning element can have a central hole as in 5-2-2 and 5-3 (FIG. 26) for the superior and inferior mandrel to center and hold it in place within the cylinder cavity 6-1-4. In other embodiments, mandrel elements 4-1 and 12-1 are eliminated and a cylindrical cushion element 5-4 (FIG. 27A) fills the entire piston cavity. The cylinder cavity protects and confines such cushioning materials, making migration and wear on the cushioning element less problematic. Hydraulic portals in the walls of the cylinder (FIG. 14) allow the flow of fluids into and out of the cushioning material as it expands and compresses, particularly if the cushioning material is hydrophilic.

In a particular embodiment, elastomer core elements 5-2-2, 5-3, 5-4 are polyurethane, polyethylene, polyetheretherketone or other thermoplastic with relative low durometer that allows compression in the range of 1 mm under a load of 130Newton. In a particular embodiment, a plurality of elastomer segments like 5-2-2 are stacked, each having different durometer and mechanical properties. In a particular embodiment, a rigid metallic or plastic washer is placed between two stacked elastomer bodies of different durometer wherein the superior surface of the inferior stacked elastomer is fixedly attached to the inferior surface of the washer and the inferior surface of the superior stacked washer is fixedly attached to the superior surface of the washer.

In a further particular embodiment, a non-linear resistance is achieved by stacking two elastomer elements 5-2-2 which are fixedly attached to each other or a washer between them. One elastomer has a higher durometer than the other. When the element with the lower durometer approaches maximum compression, the one with the higher durometer can be designed to compress further.

A real advantage of the rotating ball platform 3-1 becomes apparent as the forces acting on the spring/cushion elements will tend to be along piston axis 21. Any shear forces acting on the spring/cushion elements can be partially opposed by the cylinder walls of 6-1 acting against the ball 7-1 and inferior plate 1-1. This can considerably reduce shear stress, in particular, on elastomer elements, and, thus, reduce wear and tear.

The motion elements of the prosthetic device of the subject invention can be fabricated of for example, but not limited to, titanium steel, titanium-carbide-coated stainless steel, other biocompatible titanium alloys, such as Ti-6Al-4V, bio-inert hardened stainless steel, polyurethane, polyetheretherketone or other thermoplastic, cobalt-chromium-molybdenum alloy, high molecular density thermoplastics, ceramics, glass, or other materials or combinations thereof.

In one embodiment, thin, approximately 0.1 mm thick, titanium micro-meshes typically used in reconstructive surgery, is conformed and bonded onto convex superior surface 14-1-11 and concave inferior surface 1-1-12 to enhance surface area contact between vertebra and the plates for bone fusion.

In a further embodiment, a flexible, multi-layered boot 17-1 surrounds the prosthetic device of the subject invention. The boot provides a biocompatible impermeable barrier between fluids that may be sealed within the prosthetic device, for example, a biocompatible silicone fluid or saline solution, or other suitable fluid, and fluids within surrounding tissues. There are any of a variety of materials and designs therefor that could be utilized for the boot for embodiments of the subject invention. Such variations are contemplated to be within the scope of the subject invention.

In one embodiment, the boot is a sturdy, flexible and elastic material, such as, for example, corrugated thermoplastic materials, for example a bellows of polyurethane, woven fiber materials, and elastic materials, or other non-homogeneous materials or combinations thereof. In a preferred embodiment, the boot comprises woven, flexible fibers embedded in a strong, flexible silicon elastomer matrix that blocks fluid transfer. The embedded fiber weave, in the embodiment mentioned above, assists in torsion loading on the prosthesis, as well as loading during flexion and extension. In a further embodiment, the weave direction of the embedded fibers is diagonal relative to the central axis of a spherical or right-circular cylinder embodiment of the boot structure ("diamond" weave). In an alternative embodiment, the boot is quilted, with quilt pads filled with cushioning materials or different types of fluids/gels or beaded elastomers. In a particular embodiment, a corrugated boot, manufactured from a rugged fiber elastomer designed for flexibility and toughness, assists in torsion loading on all axes and opposes extension under nominal conditions, thus, reducing nominal spinal muscle stress in the neutral position.

In one embodiment, the boot has asymmetric thickness, using more reinforcing fiber in the posterior portion and less in the anterior portion, making the anterior portion more flexible and the posterior portion less flexible, but stronger and more durable. The non-uniformity of the boot thickness allows for non-linear compression and extension. This configuration reduces interaction with the spinal column vertebrae or surrounding nerves or ganglia when the boot is expanding and/or contracting. For example, as the FSU flexes, the boot can contract, primarily the highly flexible thinner sections. In a neutral position of the FSU, the boot can be under slight tension. At maximum compression of the FSU, the boot can bulge from hydraulic pressure and expanding cushioning material inside the device; however, without those pressures the boot would be slack. At maximum extension, the boot stretches, from its neutral position. In one embodiment, at maximum extension, the boot stretches approximately 20% in its anterior portion and approximately 10% or less in the posterior portion.

In a further embodiment, a lubricating fluid is contained within the prosthetic device of the subject invention by the impermeable boot seal. In a still further embodiment, the lubricating fluid is pumped through fluid hydraulic portals (mentioned above), or otherwise moved around and/or through the elements of the device, by the prismatic sliding action of the piston during spinal motion. The piston 25 contains spring/cushion elements 5 to assist in a spring-dashpot action during FSU workspace motion.

The low level pair joints of the devices of the subject invention can also be replaced by a variety of higher kinematic pairs by utilizing ball, rod, cylindrical and other types of bearings, known to those with skill in the art. For example, one can incorporate multiple ball-bearings partially embedded into the piston planar surface 13-1-1 of the piston head 13-1, or into planar surface 14-1-1 of the superior plate, to reduce friction forces on the planar joint motion. Bearings 6-1-7 and 7-1-4 can be replaced with ball bearings held into place by attached retention rings to facilitate motion of the cylinder prismatic joint. Ball bearings can also be embedded into surface 7-1 and/or surface 1-1-2 to facilitate ball-and-socket operation of 7-1 and 1-1. A person with skill in the art, having benefit of the subject disclosure, can determine any variety of alternative bearing structures and/or placements useful for the embodiments disclosed herein. In addition, Doty teaches in U.S. Pat. Nos. 7,361,192; 7,799,080; 7,927,375 and U.S. published patent applications US2010/0070033, PCT/US2010/37721 and US2010/0324688A1, which are all incorporated herein, in their entirety, including any figures, tables or drawings, the use of bearings to reduce friction between surfaces in similar devices.

All patents, patent applications, provisional applications, and publications referred to or cited herein are incorporated by reference in their entirety, including all figures and tables, to the extent they are not inconsistent with the explicit teachings of this specification.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

I claim:

1. A device for providing at least one and up to three rotational degrees of freedom and at least one and up to three linear degrees of freedom comprising:
a superior plate having a cranial end defined by a superior surface and a caudal end, wherein the caudal end comprises a planar socket cavity with a planar surface therein;
a piston element comprising,
a piston head having a cranial end, forming a piston planar surface, a caudal end and a lip portion therebetween, where the piston head is movably disposed within the planar socket cavity, such that the piston planar surface can slide against the planar surface and the lip portion is entirely retained within the planar socket cavity;
a neck, fixedly attached to the caudal end of the piston head;
a piston shoulder fixedly attached to the neck;
a planar retainer having a cranial end having an upper surface around a slider surface, a caudal end forming a lower surface, and a retainer hole therebetween having a diameter that is smaller than a diameter of the piston head lip portion, wherein the upper surface engages with the planar socket cavity, so that the slider surface surrounds the neck of the piston element, retaining the piston head within the planar socket cavity;
a cylinder having a cylinder wall, a cylinder planar surface, a cylinder inferior surface, a cylinder opening within the cylinder planar surface, wherein the cylinder wall has an exterior cylindrical surface with at least one bearing raceway formed therein that is orthogonal to the cylinder inferior surface and the cylinder planar surface, wherein the bearing raceway is blocked by a first bearing interlock located at or near the cylinder inferior surface, and wherein the piston shoulder is fixedly disposed within the cylinder opening;
a ball having an outer spherical surface, an interior cylindrical surface that defines a ball cavity open to a cranial end of the ball, and at least one bearing raceway formed within the interior cylindrical surface, where the cranial end of the bearing raceway is blocked by a second bearing interlock, such that the cylinder body can be disposed within the ball with the at least one bearing raceway in the exterior cylindrical surface aligned with the at least one bearing raceway in the interior cylindrical surface, such that the cylinder body can piston within the ball cavity and is prevented from exiting the cranial end of the ball cavity by interference of the first bearing interlock with the second bearing interlock;
a ball retainer with a cranial end and a caudal end having therebetween an inner spherical surface, which defines a central orifice, wherein the inner spherical surface has the same center of curvature as the outer spherical surface of the ball and an interior edge that has the same radius as the outer spherical surface of the ball, and a recess around the caudal end of the inner spherical surface, such that when the central orifice is placed over the cranial end of the ball, the interior edge abuts the outer spherical surface of the ball wherein the radii are the same, preventing the ball retainer from moving past the radius of the ball;
a ball platform having a superior surface on a cranial end and an underneath planar surface on a caudal end, a spherical segment extending from the underneath planar surface, and a peripheral spherical edge between the superior surface and the underneath planar surface, such that the caudal end of the ball and the caudal end of the cylinder body can contact the superior surface, and wherein the outer spherical surface of the ball forms a contiguous spherical surface with the spherical edge of the ball platform; and
an inferior plate having a caudal end defined by an inferior surface, an inferior cavity therein, opening at a cranial end, which has an interior spherical surface with a radius and center of curvature that are compatible with the contiguous outer spherical surface of the ball and the spherical edge of the ball platform, a lower recess around the cranial end of the inferior cavity, and a socket cavity positioned within the inferior cavity, such that when the ball platform, with the ball thereon, is placed within the inferior plate, the spherical segment of the ball platform can movably contact the socket cavity, the lower recess can be fixedly attached to the recess on the ball retainer, causing the interior spherical surface of the inferior plate to be contiguous with the spherical edge of the ball retainer, forming a slidable surface for the contiguous outer spherical surface of the ball and the ball platform,
so that the device when assembled forms a kinematic chain characterized by inseparably connected, articulating components.

2. The device, according to claim 1, further comprising one or more spring/cushion elements between one or more contacting surfaces.

3. The device, according to claim 1, wherein the cylinder further comprises a cylinder central cavity that opens to the cylinder inferior surface.

4. The device, according to claim 3, further comprising one or more spring/cushion elements within the cylinder central cavity.

5. The device, according to claim 4, wherein the one or more spring/cushion elements are one or more Belleville springs.

6. The device, according to claim 4, wherein the one or more spring/cushion elements is an elastic cylinder.

7. The device, according to claim 6, further comprising one or more Belleville springs utilized in conjunction with the elastic cylinder.

8. The device, according to claim 1, wherein one or more spring/cushion elements are positioned around the neck of the piston head.

9. The device, according to claim 8, wherein the one or more spring/cushion elements are toroidal-shaped tubes that surround the neck.

10. The device, according to claim 9, wherein the toroidal-shaped tubes are a solid material.

11. The device, according to claim 9, wherein the toroidal-shaped tubes are hollow.

12. The device, according to claim 11, wherein the toroidal-shaped tubes are filled with a gas, gel, or fluid.

13. The device, according to claim 9, wherein at least two toroidal-shaped tubes surround the neck.

14. The device, according to claim 2, wherein the one or more spring/cushion elements are positioned within the inferior cavity.

15. The device, according to claim 14, wherein the one or more spring/cushion elements are positioned between the ball platform and the inferior cavity.

16. The device, according to claim 15, wherein the one or more spring/cushion elements comprise at least one toroidal-shaped tube surrounding the socket cavity.

17. The device, according to claim 16, wherein the at least one toroidal shaped tube is solid.

18. The device, according to claim 16, wherein the toroidal-shaped tube is hollow.

19. The device, according to claim 18, wherein the toroidal-shaped tube is filed with a gas, gel, or fluid.

20. The device, according to claim 2, wherein the one or more spring/cushion elements are positioned between at least the cylinder and the ball platform.

21. The device, according to claim 20, wherein the one or more spring/cushion elements comprise a shock-absorbing washer.

22. The device, according to claim 1, further comprising one or more guide pins on the superior surface of the superior plate.

23. The device, according to claim 22, wherein the guide pins are central guide pins and/or peripheral guide pins.

24. The device, according to claim 1, further comprising one or more guide pins on the inferior surface of the inferior plate.

25. The device, according to claim 24, wherein the guide pins are central guide pins and/or peripheral guide pins.

26. The device, according to claim 25, wherein the guide pins further comprise one or more barbs, cavities, channels, tunnels, holes, indents or other types of openings, depressions, or extensions to encourage bone fusion therein and/or around.

27. The device, according to claim 25, wherein the guide pins have chamfered tips.

28. The device, according to claim 25, wherein the central guide pins are between approximately 0.25 mm and approximately 1 mm taller than the peripheral guide pins.

29. The device, according to claim 1, further comprising one or more bone fusion cavities within the superior surface of the superior plate and/or the inferior surface of the inferior plate.

30. The device, according to claim 1, wherein the bone fusion cavities are disposed at an angle relative to the plate.

31. The device, according to claim 30, wherein the angle is less than 90° relative to the plate.

32. The device, according to claim 1, further comprising one or more hydraulic portals.

33. The device, according to claim 1, wherein the distance between the superior surface and the inferior surface, during full compression, is between approximately 6 mm and approximately 10 mm.

34. The device, according to claim 1, wherein the distance between the superior surface and the inferior surface, during full extension, is between approximately 8 mm and approximately 10 mm.

35. The device, according to claim 1, wherein the ball is fixedly attached to the ball platform.

36. The device, according to claim 1, wherein the ball maintains constant contact with the superior surface of the ball platform.

37. The device, according to claim 1, wherein the cylinder comprises four bearing raceways.

38. The device, according to claim 37, wherein the ball comprises four bearing raceways.

39. The device, according to claim 1, further comprising a ledge within the inferior plate that the underneath planar surface of the ball platform can contact.

40. The device, according to claim 39, wherein the ledge dictates the rotation range of motion of the ball platform.

41. The device, according to claim 40, wherein the ledge limits rotation of the ball platform to ±10° relative to an axis perpendicular to the horizontal plane passing through the center of curvature of the socket.

42. The device, according to claim 39, further comprising a washer between the ledge and the underneath planar surface of the ball platform.

43. The device, according to claim 1, further comprising a boot fixedly attached to the superior plate and the inferior plate.

44. The device, according to claim 43, wherein the boot comprises a flexible, fiber-reinforced material.

45. The device, according to claim 44, wherein the boot isolates the articulating components from contact with external materials.

46. The device, according to claim 45, wherein the fiber-reinforcement has a diamond-weave pattern.

47. The device, according to claim 43, further comprising at least one groove within the superior plate and one groove within the inferior plate in which the boot can be attached therebetween.

48. The device, according to claim 43, further comprising one or more clamping rings/band for securing the boot within the grooves.

49. The device, according to claim 48, further comprising one or more grooves within the boot that can be aligned with the grooves of the superior plate and/or the inferior plate.

50. The device, according to claim 43, further comprising an adhesive sealant between the boot and the superior plate and/or the inferior plate.

51. The device, according to claim 43, wherein the boot has an asymmetric thickness, such that some portion comprises more material and is thicker than another portion, causing the thicker portion to be less flexible.

52. The device, according to claim 44, wherein the boot comprises a flexible silicone elastomer matrix material.

53. The device, according to claim 1, further comprising a multi-layer boot fixedly attached to the superior plate and the inferior plate.

54. The device, according to claim 53, wherein at least one layer is a flexible elastomer material.

55. The device, according to claim 54, wherein at least one layer is fiber woven material.

56. The device, according to claim 55, wherein the material isolates the articulating components from contact with external materials.

57. The device, according to claim 56, wherein the fiber-woven material has a diamond-weave pattern.

58. The device, according to claim 53, further comprising at least one groove within the superior plate and one groove within the inferior plate in which the multi-layer boot can be attached therebetween.

59. The device, according to claim 53, further comprising one or more clamping rings/bands for securing the multi-layer boot within the grooves.

60. The device, according to claim 59, further comprising one or more grooves within the multi-layer boot that can be aligned with the grooves of the superior plate and the inferior plate.

61. The device, according to claim 60, further comprising an adhesive sealant between the boot and the superior plate and/or the inferior plate.

62. The device, according to claim 53, wherein the boot has an asymmetric thickness, such that some portion comprises more material and is thicker than another portion, causing the thicker portion to be less flexible.

63. The device, according to claim 54, wherein the flexible elastomer material comprises a flexible silicone elastomer matrix material.

64. The device, according to claim 3, wherein the cylinder central cavity is contiguous with the cylinder opening and further comprises:
a superior mandrel having one or more wall segments, with slots therebetween, wherein each wall segment has a cranial end and a caudal end, such that the cranial end is fixedly attached to and/or integrated with a caudal end of the piston shoulder and the wall segments extend caudally into the central cylinder cavity; and
an inferior mandrel having a central core with one or more fixedly attached and/or integrated wall segments, with slots therebetween, wherein each wall segment has a cranial end and a caudal end, such that the caudal end is fixedly attached to the superior surface of the ball platform and the wall segments extend cranially into the central cylinder cavity,
wherein the wall segments of the superior mandrel slidingly engage with the slots between the wall segments of the inferior mandrel, such that the mandrel wall segments mesh and slide past one another on a central axis of the cylinder.

65. The device, according to claim 64, wherein the superior mandrel and the inferior mandrel are inseparable, even at maximum extension of the device.

66. The device, according to claim 65, further comprising one or more spring/cushion elements within the cylinder central cavity.

67. The device, according to claim 66, wherein spring/cushion elements are one or more elastomer cushion elements.

68. The device, according to claim 67, wherein the elastomer cushion element surrounds the superior mandrel wall segments and the inferior mandrel wall segments.

69. The device, according to claim 66, wherein the one or more spring/cushion elements are one or more Belleville springs.

70. The device, according to claim 69, wherein the Belleville springs surround the superior mandrel wall segments and the inferior mandrel wall segments.

71. The device, according to claim 66, wherein the wall segments of the superior mandrel are chamfered, or otherwise tapered, at their caudal ends.

72. The device, according to claim 65, wherein the superior mandrel comprises at least two wall segments and the inferior mandrel comprises at least two wall segments.

73. The device, according to claim 65, wherein the superior mandrel comprises at least three wall segments and the inferior mandrel comprises at least three wall segments.

74. A method for approximating spinal disc movement comprising:
implanting within the spine of a patient a prosthetic device comprising:
a superior plate having a cranial end defined by a superior surface and a caudal end, wherein the caudal end comprises a planar socket cavity with a planar surface therein;
a piston element comprising,
a piston head having a cranial end, forming a piston planar surface, a caudal end and a lip portion therebetween, wherein the piston head is movably disposed within the planar socket cavity, such that the piston planar surface can slide against the planar surface and the lip portion is entirely retained within the planar socket cavity;
a neck, fixedly attached to the caudal end of the piston head;
a piston shoulder fixedly attached to the neck;
a planar retainer having a cranial end having an upper surface around a slider surface, a caudal end forming a lower surface, and a retainer hole therebetween having a diameter that is smaller than a diameter of the piston head lip portion, wherein the upper surface engages with the planar socket cavity, so that the slider surface surrounds the neck of the piston element, retaining the piston head within the planar socket cavity;
a cylinder having a cylinder wall, a cylinder planar surface, a cylinder inferior surface, a cylinder opening within the cylinder planar surface, where the cylinder wall has an exterior cylindrical surface with at least one bearing raceway formed therein that is orthogonal to the cylinder inferior surface and the cylinder planar surface, wherein the bearing raceway is blocked by a first bearing interlock located at or near the cylinder inferior surface, and wherein the piston shoulder is fixedly disposed within the cylinder opening;
a ball having an outer spherical surface, an interior cylindrical surface that defines a ball cavity open to a cranial end of the ball, and at least one bearing raceway formed within the interior cylindrical surface, where the cranial end of the hearing raceway is blocked by a second bearing interlock, such that the cylinder body can be disposed within the ball with the at least one bearing raceway in the exterior cylindrical surface aligned with the at least one bearing raceway in the interior cylindrical surface, such that the cylinder body can piston within the ball cavity and is prevented from exiting the cranial end of the ball cavity by interference of the first bearing interlock with the second bearing interlock;
a ball retainer with a cranial end and a caudal end having therebetween an inner spherical surface, which defines a central orifice, wherein the inner spherical surface has the same center of curvature as the outer spherical surface of the ball and an interior edge that has the same radius as the outer spherical surface of the ball, and a recess around the caudal end of the inner spherical surface, such that when the central orifice is placed over the cranial end of the ball, the interior edge abuts the outer spherical surface of the ball wherein the radii are the same, preventing the ball retainer from moving past the radius of the ball;
a ball platform having a superior surface on a cranial end and an underneath planar surface on a caudal end, a spherical segment extending from the underneath planar surface, and a peripheral spherical edge between the superior surface and the underneath planar surface, such that the caudal end of the ball and the caudal end of the cylinder body can contact the superior surface, and wherein the outer spherical surface of the ball forms a contiguous spherical surface with the spherical edge of the ball platform; and an inferior plate having a caudal end defined by an inferior surface, an inferior cavity therein, opening at a cranial end, which has an interior spherical surface with a radius and center of curvature that are compatible with the contiguous outer spherical surface of the ball and the spherical edge of the ball platform, a lower recess around the cranial end of the inferior cavity, and a socket cavity positioned within the inferior cavity, such that when the ball platform, with the ball thereon, is placed within the inferior plate, the spherical segment of the ball platform can movably contact the socket cavity, the lower recess can be fixedly attached to the recess on the ball retainer, causing the interior spherical surface of the inferior plate to be contiguous with the spherical edge of the ball retainer, forming a slidable surface for the contiguous outer spherical surface of the ball and the ball platform, such that when said device is implanted in the spine with the superior and inferior vertebral plates engaged with a first and second vertebra, said device forms a kinematic chain of connected, inseparable, articulating components between said first and second vertebra, thereby providing at least one and up to three independent rotational degrees of freedom and at least one and up to three independent linear degrees of freedom.

75. The method, according to claim 74, wherein the device is implanted within a patient with the superior vertebral plate more cranial than the inferior vertebral plate.

* * * * *

UNITED STATES PATENT AND TRADEMARK OFFICE
CERTIFICATE OF CORRECTION

| | | |
|---|---|---|
| PATENT NO. | : 8,287,598 B1 | Page 1 of 1 |
| APPLICATION NO. | : 13/311135 | |
| DATED | : October 16, 2012 | |
| INVENTOR(S) | : Keith L. Doty | |

It is certified that error appears in the above-identified patent and that said Letters Patent is hereby corrected as shown below:

Column 14,
Line 29, "$2^{nd}$ Addition" should read --$2^{nd}$ Edition--.

Column 15,
Line 26, "The hoot" should read --The boot--.

Column 22,
Line 55, "fixed hearings" should read --fixed bearings--.

Column 27,
Line 59, "almost 2 h" should read --almost 2h--.

Column 29,
Line 54, "hearing interlocks" should read --bearing interlocks--.

Column 34,
Line 10, "surface 1-142" should read --surface 1-1-12--.

Column 37,
Lines 64-65, "hearing raceway" should read --bearing raceway--.

Column 39,
Line 27, "is filed with" should read --is filled with--.

Column 42,
Line 44, "hearing raceway" should read --bearing raceway--.

Signed and Sealed this
Fifteenth Day of January, 2013

David J. Kappos
*Director of the United States Patent and Trademark Office*